US011859106B2

(12) United States Patent
Samanta et al.

(10) Patent No.: US 11,859,106 B2
(45) Date of Patent: Jan. 2, 2024

(54) PIGMENT DISPERSANT

(71) Applicant: BASF Coatings GmbH, Münster (DE)

(72) Inventors: Shampa R. Samanta, Southfield, MI (US); Chintankumar Patel, Mangalore (IN); Colin Wade, Southfield, MI (US); Benjamin Georg Robert Mohr, Ludwigshafen (DE)

(73) Assignee: BASF COATINGS GMBH, Muenster (DE)

( * ) Notice: Subject to any disclaimer, the term of this patent is extended or adjusted under 35 U.S.C. 154(b) by 280 days.

(21) Appl. No.: 17/270,496

(22) PCT Filed: Aug. 8, 2019

(86) PCT No.: PCT/EP2019/071293
§ 371 (c)(1),
(2) Date: Feb. 23, 2021

(87) PCT Pub. No.: WO2020/043453
PCT Pub. Date: Mar. 5, 2020

(65) Prior Publication Data
US 2021/0324210 A1  Oct. 21, 2021

(30) Foreign Application Priority Data
Aug. 29, 2018 (EP) ..................... 18191460

(51) Int. Cl.
| *C09D 7/65* | (2018.01) |
| *C08F 220/18* | (2006.01) |
| *C08F 220/32* | (2006.01) |
| *C08F 212/08* | (2006.01) |
| *C08F 220/20* | (2006.01) |
| *C08F 265/04* | (2006.01) |
| *C08F 293/00* | (2006.01) |
| *C08K 5/09* | (2006.01) |
| *C08K 5/3417* | (2006.01) |
| *C09D 11/10* | (2014.01) |
| *C09D 17/00* | (2006.01) |

(52) U.S. Cl.
CPC .............. *C09D 7/65* (2018.01); *C08F 212/08* (2013.01); *C08F 220/1804* (2020.02); *C08F 220/1808* (2020.02); *C08F 220/20* (2013.01); *C08F 220/325* (2020.02); *C08F 265/04* (2013.01); *C08F 293/005* (2013.01); *C08K 5/09* (2013.01); *C08K 5/3417* (2013.01); *C09D 11/10* (2013.01); *C09D 17/001* (2013.01); *C09D 17/002* (2013.01)

(58) Field of Classification Search
None
See application file for complete search history.

(56) References Cited

U.S. PATENT DOCUMENTS

| 5,763,548 | A | 6/1998 | Matyjaszewski et al. |
| 5,789,487 | A | 8/1998 | Matyjaszewski et al. |
| 5,807,937 | A | 9/1998 | Matyjaszewski et al. |
| 6,037,414 | A | 3/2000 | Simms et al. |
| 6,365,666 | B1 | 4/2002 | McCollum et al. |
| 6,642,301 | B2 | 11/2003 | White et al. |
| 7,265,197 | B2 * | 9/2007 | Huber ..................... C08L 59/00 523/160 |
| 7,723,425 | B2 | 5/2010 | Auschra et al. |
| 8,129,466 | B2 | 3/2012 | Polk et al. |
| 9,534,123 | B2 * | 1/2017 | Shooter .............. C08G 73/1075 |
| 2005/0120911 | A1 | 6/2005 | Huber et al. |
| 2016/0257774 | A1 * | 9/2016 | Shooter ............... C08F 290/067 |

FOREIGN PATENT DOCUMENTS

| CN | 107674205 A | 2/2018 |
| GB | 1297191 A | 11/1972 |
| JP | 57123209 A * | 7/1982 |
| JP | S57123209 A | 7/1982 |
| JP | H02292332 A | 12/1990 |
| WO | 9840415 A1 | 9/1998 |
| WO | 2004079012 A1 | 9/2004 |
| WO | 2008028954 A2 | 3/2008 |
| WO | 2009039635 A1 | 4/2009 |
| WO | 2015066163 A1 | 5/2015 |

OTHER PUBLICATIONS

JP 57-123209 , Jul. 1982, Partial translation (Year: 1982).*
Behniafar, et al., "New heat stable and processable poly(amide ether-imide)s derived from 5-(4- trimellitimidophenoxy)-1-trimellitimido naphthalene and various diamines", Polymer Degradation and Stability, vol. 93, Issue 3, Mar. 2008, pp. 608-617.
Behniafar, et al., "Thermally stable and organosoluble cardo binaphthylene based poly(amide imide)s and poly (ester imide)s", Journal of Applied Polymer Science, vol. 100, Issue 4, Feb. 27, 2006, pp. 3203-3211.
European Search Report for EP Patent Application No. 18191460.7, dated Mar. 11, 2019, 5 pages.
Fritsch, et al., "Synthesis and properties of highly gas permeable poly(amide-imide)s", Macromolecular Chemistry and Physics, vol. 197, Issue 2, Feb. 1996, pp. 701-714.
Mehdipour-Ataei, et al., "Preparation of poly(ether amide imide)s from five different methods and investigation of properties", Reactive and Functional Polymers, vol. 66, Issue 4, Apr. 2006, pp. 403-412.
Ruzicka, et al., "Polyterpene und Polyterpenoide LXXXIX. Synthese der Heptan-2,5,6-tricarbonsäure, eines Abbauproduktes des Santonins", Helvetica Chimica Acta, vol. 17, Issue 1, 1934, pp. 614-621.
Thiruvasagam, et al., "Synthesis of poly(amide-imide)s from new diacid monomers: Study of structure-property relationship and applications", High Performance Polymers, vol. 24, Issue 3, Apr. 9, 2012, pp. 210-217.

(Continued)

*Primary Examiner* — Satya B Sastri
(74) *Attorney, Agent, or Firm* — Armstrong Teasdale LLP

(57) ABSTRACT

Described herein is a polymeric pigment dispersant, a process for preparation of the polymeric pigment dispersant, and a pigment dispersion including the pigment dispersant that is used for coating and in printing ink, automotive basecoat, automotive clearcoat, mill base, furniture coatings, and wood coatings.

12 Claims, No Drawings

(56) References Cited

OTHER PUBLICATIONS

Yang, et al., "Synthesis and properties of poly(amide-imide)s based on 1,5-bis(4-trimellitimido)naphthalene", Journal of Polymer Research, vol. 5, Issue 1, Jan. 1998, pp. 23-29.
International Search Report and Written Opinion for corresponding PCT/EP2019/071293 dated Sep. 27, 2019, 13 Pages.
"CA, Caplus", Cas Registry No. RN:2231070-56-5, Jul. 19, 2018, p. 1.

* cited by examiner

PIGMENT DISPERSANT

CROSS-REFERENCE TO RELATED APPLICATIONS

This application is a U.S. National Phase Application of International Patent Application No. PCT/EP2019/071293, filed Aug. 8, 2019, which claims the benefit of priority to European Patent Application No. 18191460.7, filed Aug. 29, 2018, the entire contents of which are hereby incorporated by reference herein.

TECHNICAL FIELD

The presently claimed invention relates to a polymeric pigment dispersant, a process for preparation of the polymeric pigment dispersant and a pigment dispersion comprising the pigment dispersant that is used for coating and in printing ink, automotive basecoat, automotive clearcoat, mill base, furniture coatings and wood coatings. The presently claimed invention further relates to a coating composition comprising the pigment dispersion.

BACKGROUND

Pigmented coating compositions are widely used as corrosion resistant primers and decorative topcoats in automotive industry. The automotive market is trending toward high transparency colour and rich chroma as colour is a major factor in the vehicle-commercialization segment of the automotive industry. The high transparency and the rich chroma is generally achieved by very stable fine dispersion of organic pigment to the submicron size in the clearcoat. But the agglomeration of the pigment particles of small size, i.e. below 100 nm, during their application in coating and in long term storage in the coating composition is a major challenge in the coating industry. It is desirable that the pigment dispersions remain substantially stable with minimal pigment stalling and viscosity change.

Traditionally, random copolymers used in pigment dispersion compositions contain multiple anchoring and stabilizing segments and their application as dispersants do not provide adequate stabilization, especially when the particle size is small. Further, hyperdispersants available in the market have controlled architecture which has several limitations such as a specific set-up and the conditions for their synthesis. Alternatively, amines are used as anchoring moieties in commercial dispersants to stabilize the pigment particles through acid-base reaction or hydrogen bonding. But the amines react with the acid catalyst present in the clearcoat composition resulting in the precipitation of the pigments. Therefore, there is a need for continued development of pigment dispersions to address the problems of the existing pigment dispersion compositions.

In the state of the art, hyperdispersant with controlled architecture and pigment dispersant comprising imide anchoring blocks are known and described, for instance, in the following references.

U.S. 2016/257774 A1 describes a polymeric dispersant composition comprising an acrylic backbone with at least one pendantly attached imide group, wherein the carbonyl of the imide is chemically bonded to a fused aromatic ring.

U.S. Pat. No. 6,037,414 A describes a polymeric pigment dispersant comprising a graft polymer having an acrylic backbone, polyester side chains, cyclic imide groups and quaternary ammonium groups.

U.S. Pat. No. 8,129,466 B2 describes a nanoparticle dispersion comprising a dispersant comprising a tri-block polymer having a first block comprising a glycidyl(meth)acrylate reacted with a naphthoic acid, a second block comprising (meth)acrylic acid alkyl esters, and a third block comprising (meth)acrylic acid alkyl esters, wherein said third block is different from said second block.

U.S. Pat. No. 7,723,425 B2 describes a composition containing modified block copolymer dispersants prepared by atom transfer radical polymerisation (ATRP) and modified with a salt forming group. The salt forming group is selected from specific monocyclic sulphonic acids or polycyclic sulphonic acids or mono- or polycyclic carboxylic and phosphonic acids, or alkyl halogenide containing monocyclic or polycyclic groups or esters of monocyclic or polycyclic sulphonic acids.

The methods and compositions disclosed in the prior arts have limitations. The compositions described in the prior arts described above do not provide efficient pigment dispersants that provide effective de-agglomeration and strong interaction with the pigment particles to achieve a fine dispersion of the pigment particles to the submicron size. The absence of a strong interaction with the pigment particles affects the transparency and colour which is desired in the market. Since, the demand for niche colour spaces with high saturation is increasing in the coating and ink market, there is a need for the synthesis of novel pigment dispersions that overcome the above-mentioned drawbacks and include a robust anchoring block that can interact with aromatic pigment molecules via $\pi$-$\pi$ interaction and hydrogen bonding interaction.

Hence, it is an object of the presently claimed invention to provide a pigment dispersant and a pigment dispersion comprising the pigment dispersant having well-defined polymer chain architecture that provides efficient dispersion of the pigment particles as evidenced by the lower lightness (determined by measurement of L* value) of the coating resulting from the pigment dispersion containing the polymeric pigment dispersant which can easily be synthesized under mild conditions.

A further object of the presently claimed invention is to provide an efficient process to prepare the polymeric pigment dispersant.

SUMMARY

Surprisingly, it was found that the coating compositions comprising a novel polymeric pigment dispersant as described hereinbelow provides excellent stabilization to the pigment particles as evidenced by the lower lightness (determined by measurement of L* value) of the coating resulting from the coating compositions comprising the novel polymeric pigment dispersant. Further, it was unexpectedly found that the process of preparation of the polymeric pigment dispersant as described hereinbelow is more efficient and less expensive than the traditionally known methods to synthesize polymeric pigment dispersants.

Accordingly, in one aspect, the presently claimed invention is directed to a polymeric pigment dispersant comprising a polymer backbone (P) and at least one moiety of the formula (I):

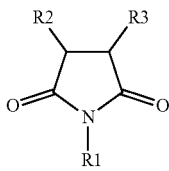

(I)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or a branched, substituted $C_2$-$C_{14}$ alkenyl, which are each substituted with one —C(=O)—O— group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—O— group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—O— group; and whereby the moiety of the formula (I) is bonded to the polymer backbone (P) via the —C(=O)—O— group.

In another aspect, the presently claimed invention is directed to a process for the preparation of at least one polymeric pigment dispersant comprising at least the steps of:
reacting a linear di-block polymer with a compound of the formula (IV):

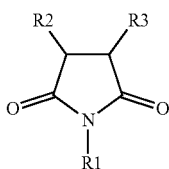

(IV)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—OH group;
at a temperature from ≥80° C. to ≤150° C.; and
wherein the linear di-block polymer comprises a first and a second block and is obtained by a living free radical polymerization, optionally in the presence of a solvent.

In yet another aspect, the presently claimed invention is directed to a process for the preparation of at least one polymeric pigment dispersant comprising at least the steps of:

(a) reacting a random polymer with a compound of the formula (IV):

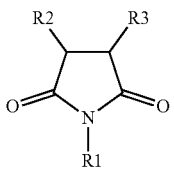

(IV)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—OH group;
and
(b) reacting the compound obtained in step (a) with at least one monomer of a lactone at a temperature from ≥30° C. to ≤190° C.

In another aspect, the presently claimed invention is directed to a process for the preparation of at least one polymeric pigment dispersant comprising at least the steps of:
(a) reacting at least one polyalkylene glycol monoalkyl ether and at least one carboxylic acid anhydride at a temperature in the range from ≥70° C. to ≤140° C. to obtain a mixture; and
(b) reacting the mixture obtained in step (a) with a random polymer and a compound of the formula (IV):

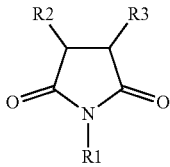

(IV)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—OH group;
at a temperature in the range from ≥70° C. to ≤140° C.

In another aspect, the presently claimed invention is directed to a pigment dispersion comprising at least one polymeric pigment dispersant according to the presently claimed invention, at least one solvent and at least one pigment.

In another aspect, the presently claimed invention is directed to a coating composition comprising the pigment dispersion according to the presently claimed invention and at least one binder.

In another aspect, the presently claimed invention is directed to a use of the pigment dispersion according to the presently claimed invention in printing ink, automotive basecoat, automotive clearcoat, mill base, furniture coatings and wood coatings.

In yet another aspect, the presently claimed invention is directed to an article coated with at least one layer formed from the coating composition according to the presently claimed invention.

In another aspect, the presently claimed invention is directed to a compound of formula (IV)

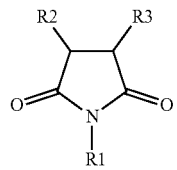

(IV)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl which are each substituted with one —C(=O)—OH group;
whereby the following compound N-napthalenyl-4-carboxy-1,2-phthalimide is excluded.

In another aspect, the presently claimed invention is directed to a compound of formula (IV)

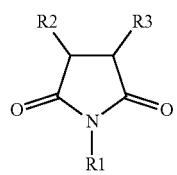

(IV)

wherein
R1 is selected from the group consisting of unsubstituted naphthyl or naphthyl substituted with 1, 2 or 3 —OH; and R2 and R3 together with the carbon atoms to which they are bonded form a ring selected from the group consisting of phenyl and cyclohexyl which are each substituted with one —C(=O)—OH group.

The presently claimed invention is associated with at least one of the following advantages:
(i) the polymeric pigment dispersants are synthesized with di-block and random polymer architecture using conventional polymerization technique,
(ii) pigment dispersions with pigment particles of submicron particle size of less than 100 nm are provided,
(iii) the compounds of formula (IV) as described hereinbelow provides good interaction and strong adsorption with a pigment surface by even weak interactions like π-π and hydrogen bonding interaction,
(iv) the compounds of formula (IV) as described hereinbelow has increased solubility in low polarity solvents,
(v) the polymer backbone (P) of the presently claimed invention provides steric stabilization,
(vi) the polymeric pigment dispersants of the presently claimed invention provides high chroma and transparent colour in comparison to traditional hyperdispersants, and
(vii) the polymeric pigment dispersants of the presently claimed invention do not interact with a strong acid catalyst and is therefore compatible with clearcoat compositions containing organic acid catalyst.

Other objects, advantages and applications of the presently claimed invention will become apparent to those skilled in the art from the following detailed description.

DETAILED DESCRIPTION

The following detailed description is merely exemplary in nature and is not intended to limit the presently claimed invention or the application and uses of the presently claimed invention. Furthermore, there is no intention to be bound by any theory presented in the preceding technical field, background, summary or the following detailed description.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

Furthermore, the terms "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the subject matter described herein are capable of operation in other sequences than described or illustrated herein. In case the terms "(A)", "(B)" and "(C)" or "(a)", "(b)", "(c)", "(d)", "(i)", "(ii)" etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

In the following passages, different aspects of the subject matter are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the presently claimed invention. Thus, appearances of the phrases "in one embodiment" or "in an embodiment" in various places throughout this specification are not necessarily all referring to the same embodiment but may refer. Furthermore, the features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the subject matter, and form different embodiments, as would be understood by those in the art. For example, in the appended claims, any of the claimed embodiments can be used in any combination.

Furthermore, the ranges defined throughout the specification include the end values as well, i.e. a range of 1 to 10 implies that both 1 and 10 are included in the range. For the avoidance of doubt, the applicant shall be entitled to any equivalents according to applicable law.

For the purposes of the presently claimed invention, a block polymer or a block copolymer is defined as a polymer or a copolymer formed, when two or more monomers cluster together and form 'blocks' of repeating units.

For the purposes of the presently claimed invention, a random polymer or a random copolymer is defined as a polymer or a copolymer formed, when two or more monomers are added as repeating units in a completely random manner.

For the purposes of the presently claimed invention, a graft polymer is a segmented copolymer with a linear backbone of one composite and randomly distributed branches of another composite.

Reference throughout this specification to the term "copolymer" means that the copolymer comprises block or random copolymers obtainable by radical polymerization.

For the purposes of the presently claimed invention, the mass-average ($M_w$) and number-average ($M_n$) molecular weight is determined by means of gel permeation chromatography at 40° C., using a high-performance liquid chromatography pump and a refractive index detector. The eluent used was tetrahydrofuran with an elution rate of 1 ml/min. The calibration is carried out by means of polystyrene standards.

For the purposes of the presently claimed subject matter, a polar solvent is defined to be a solvent with large dipole moments and which contains bonds between atoms with very different electronegativities.

For the purposes of the presently claimed invention, a dielectric constant value of a solvent indicates a measure of polarity of the solvent. Higher dielectric constant of a solvent is indicative of more polarity of the solvent.

For the purposes of the presently claimed invention, a use of (meth) in a monomer or repeat unit indicates an optional methyl group.

For the purposes of the presently claimed invention, transparent or transparency is defined as a property of a material to allow visible light completely or partially to pass through the material without being scattered.

For the purposes of the presently claimed invention, a pigment is defined to be any substance that alters the colour of a material through selective absorption or any substance that scatters and reflects light.

For the purposes of the presently claimed invention, effect pigments are defined as flake or platy structures that impart a directional light reflectance, scattering, absorption, or optically variable appearance to the substrate in or on which they are applied.

For the purposes of the presently claimed invention, polydispersity or polydispersity index (PDI) is defined to be a measure of the distribution of molecular mass in a given polymer.

For the purposes of the presently claimed invention, '%' by weight' or 'wt. %' as used in the presently claimed invention is with respect to the total weight of the coating composition. Further, sum of wt.-% of all the compounds, as described hereinbelow, in the respective component adds up to 100 wt.-%.

The above-mentioned measurement techniques are well known to a person skilled in the art and therefore do not limit the presently claimed invention.

Polymeric Pigment Dispersant

An aspect of the presently claimed invention describes a polymeric pigment dispersant comprising a polymer backbone (P) and at least one moiety of the formula (I):

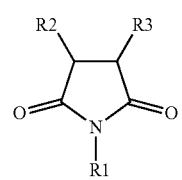

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or a branched, substituted $C_2$-$C_{14}$ alkenyl, which are each substituted with one —C(═O)—O— group;
R3 is selected from the group consisting of a linear or a branched, substituted $C_1$-$C_{14}$ alkyl and a linear or branched, substituted $C_2$-$C_{14}$ alkenyl, which are each substituted with one —C(═O)—O— group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(═O)—O— group; and
whereby the moiety of the formula (I) is bonded to the polymer backbone (P) via the —C(═O)—O— group.

In an embodiment of the presently claimed invention, the R1 in formula (I) described hereinabove is selected from the group consisting of naphthyl, anthracenyl and phenanthrenyl which are unsubstituted or substituted with F, Cl, Br, I, —NO₂, —CN, —OH, —O—$C_1$-$C_6$-alkyl, —C(═O)—$C_1$-$C_6$-alkyl, —C(═O)—O—$C_1$-$C_6$-alkyl, —C(═O)—O-phenyl, —CH₂—C(═O)—$C_1$-$C_6$-alkyl, —C(═O)—NH($C_1$-$C_6$)alkyl, —C(═O)—NH-phenyl, —$C_1$-$C_6$-alkyl; wherein —$C_1$-$C_6$-alkyl is itself unsubstituted or substituted with 1, 2, 3, 4 or 5 substituents independently of each other selected from the group consisting of F, Cl, Br, I, —CN, —OH, —O—CF₃, —O—CH₃ and —O—$C_2H_5$.

In a preferred embodiment of the presently claimed invention, R1 in formula (I) described hereinabove is naphthyl which is unsubstituted or substituted with 1, 2, 3, 4 or 5 substituents independently of each other selected from the group consisting of F, Cl, Br, I, —$NO_2$, —CN, —OH, —O—$C_1$-$C_6$-alkyl, —C(=O)—$C_1$-$C_6$-alkyl, —C(=O)—O—$C_1$-$C_6$-alkyl, —C(=O)—O-phenyl, —$CH_2$—C(=O)—$C_1$-$C_6$-alkyl, —C(=O)—NH($C_1$-$C_6$)alkyl, —C(=O)—NH-phenyl, —$C_1$-$C_6$-alkyl; wherein —$C_1$-$C_6$-alkyl is itself unsubstituted or substituted with 1, 2, 3, 4 or 5 substituents independently of each other selected from the group consisting of F, Cl, Br, I, —CN, —OH, —O—$CF_3$, —O—$CH_3$ and —O—$C_2H_5$.

In a preferred embodiment of the presently claimed invention, R1 in formula (I) described hereinabove is selected from the group consisting of naphthyl, anthracenyl and phenanthrenyl which are each unsubstituted or substituted with 1, 2 or 3 —OH.

In a preferred embodiment of the presently claimed invention, R2 and R3 in formula (I) described hereinabove together with the carbon atoms to which they are bonded form a ring selected from the group consisting of phenyl and cyclohexyl which are each substituted with one —C(=O)—O— group.

In another embodiment of the presently claimed invention, the at least one moiety of the formula (I) and the compound of general formula (IV), respectively, are obtained by reacting at least one compound of formula (II)

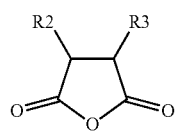

wherein
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl which are each substituted with one —C(=O)—OH group;
with at least one compound of formula (III)

 R1-$NH_2$ (III)

wherein
R1 is selected from the group consisting of unsubstituted or substituted naphthyl, unsubstituted or substituted anthracenyl and unsubstituted or substituted phenanthrenyl;
optionally in the presence of at least one solvent (S1).

In a preferred embodiment of the presently claimed invention, the at least one compound of formula (II) described hereinabove is selected from the group consisting of phthalic anhydride, hexahydrophthalic anhydride, dodecenyl succinic anhydride, octadecenyl succinic anhydride, tetrahydrophthalic anhydride, methyltetrahydrophthalic anhydride and endomethylene tetrahydrophthalic, which are each substituted with one —C(=O)—OH group. In a more preferred embodiment of the presently claimed invention, the at least one compound of formula (II) described hereinabove is selected from the group consisting of 1,2,4-benzenetricarboxylic anhydride and 1,2-cyclohexanecarboxylic anhydride.

In a preferred embodiment of the presently claimed invention, the at least one compound of formula (III) described hereinabove is selected from the group consisting of 1-naphthylamine and 7-hydroxy 1-naphthylamine.

In another embodiment of the presently claimed invention, the at least one solvent (S1) is a polar solvent having a boiling point in the range of ≥80° C. to ≤160° C. and a dielectric constant in the range of ≥11 to ≤30.

In a preferred embodiment of the presently claimed invention, the at least one solvent (S1) is a polar solvent having a boiling point in the range of ≥80° C. to ≤130° C. and a dielectric constant in the range of ≥11 to ≤25.

In a preferred embodiment of the presently claimed invention, the at least one solvent (S1) is selected from the group consisting of methyl N-amyl ketone, ethyl methyl ketone, methyl isoamyl ketone and isopropanol.

For the purposes of the presently claimed invention, the compound of general formula (IV) can be more preferably synthesized by the reaction described hereinabove in the presence of less polar and lower boiling solvents like isopropanol, ethyl methyl ketone, methyl isoamyl ketone and methyl N-amyl ketone.

In an embodiment of the presently claimed invention, the polymeric pigment dispersant has a number average molecular weight ($M_n$) in the range of from ≥1000 g/mol to ≤25000 g/mol, determined according to gel permeation chromatography against a polystyrene standard. In a preferred embodiment of the presently claimed invention, the polymeric pigment dispersant has a number average molecular weight ($M_n$) in the range of from ≥1000 g/mol to ≤15000 g/mol.

In an embodiment of the presently claimed invention, the polymeric pigment dispersant has a polydispersity in the range of from ≥1.2 to ≤20, determined according to gel permeation chromatography against a polystyrene standard. In another embodiment of the presently claimed invention, the polymeric pigment dispersant has a polydispersity in the range of from ≥1.2 to ≤10, determined according to gel permeation chromatography against a polystyrene standard. In a preferred embodiment of the presently claimed invention, the polymeric pigment dispersant has a polydispersity in the range of from ≥1.2 to ≤3.5, determined according to gel permeation chromatography against a polystyrene standard. In a most preferred embodiment of the presently claimed invention, the polymeric pigment dispersant has a polydispersity in the range of from ≥1.2 to ≤2.2, determined according to gel permeation chromatography against a polystyrene standard.

In an embodiment of the presently claimed invention, the total weight of the at least one moiety of the formula (I) is in the range of from ≥5 wt. % to ≤50 wt. %, based on the total weight of the polymeric pigment dispersant. In a preferred embodiment of the presently claimed invention, the total weight of the at least one moiety of the formula (I) is in the range of from ≥5 wt. % to ≤30 wt. %, based on the total weight of the polymeric pigment dispersant.

Linear Di-Block Polymer

In an embodiment of the presently claimed invention, the polymer backbone (P) described hereinabove is a linear di-block polymer.

In another embodiment of the presently claimed invention, the linear di-block polymer is obtained by a living free radical polymerization.

In an embodiment of the presently claimed invention, the linear di-block polymer is obtained by a living free radical polymerization referred to as atom transfer radical polymerization (ATRP).

The ATRP process is described to provide highly uniform products having controlled structure and is also referred to as controlled radical polymerization (CRP). The ATRP process is described for preparation of copolymers which are useful in a wide variety of applications, including pigment dispersant in U.S. Pat. Nos. 6,365,666 B1 and 6,642,301 B2. The ATRP process description can be found in detail in U.S. Pat. Nos. 5,807,937 A, 5,763,548 A, 5,789,487 A and WO 1998/40415 A1.

For purposes of the presently claimed invention, the linear di-block polymer can be obtained by other polymerization techniques like reversible addition-fragmentation chain transfer (RAFT) polymerization, single electron transfer living radical polymerization (SEL-LRP), nitroxide mediated radical polymerization (NMRP), living ring opening metathesis polymerization (ROMP), living anionic and living cationic polymerization.

In a yet another embodiment of the presently claimed invention, the linear di-block polymer has a formula A-B, wherein A is a first polymer block which is obtained by reacting a first mixture comprising at least one glycidyl (meth)acrylate; and B is a second polymer block which is obtained by reacting a second mixture comprising at least one monomer selected from the group consisting of alkyl (meth)acrylate, hydroxyalkyl (meth)acrylate, polyethylene glycol (meth)acrylate and polyethylene glycol alkyl ether (meth)acrylate.

In an embodiment of the presently claimed invention, the linear di-block polymer A-B is obtained by reacting the first polymer block A and the second polymer block B, optionally in the presence of at least one solvent and optionally in the presence of at least one catalyst.

In another embodiment of the presently claimed invention, the linear di-block polymer has a formula A-B, wherein A is a first polymer block which is obtained by reacting a first mixture comprising at least one glycidyl (meth)acrylate; and B is a second polymer block which is obtained by reacting a second mixture comprising at least one monomer selected from the group consisting of alkyl (meth)acrylate, hydroxyalkyl (meth)acrylate, polyethylene glycol (meth)acrylate and polyethylene glycol alkyl ether (meth)acrylate;

optionally in the presence of at least one solvent.

In a preferred embodiment of the presently claimed invention, the first polymer block A described hereinabove is obtained by reacting a first mixture comprising at least one glycidyl (meth)acrylate.

In a preferred embodiment of the presently claimed invention, the second polymer block B described hereinabove is obtained by reacting a second mixture comprising at least one monomer of alkyl (meth)acrylate, at least one monomer of hydroxyalkyl (meth)acrylate, at least one monomer of polyethylene glycol (meth)acrylate and at least one monomer of polyethylene glycol alkyl ether (meth)acrylate.

In a preferred embodiment of the presently claimed invention, the second polymer block B described hereinabove is obtained by reacting a second mixture comprising at least one monomer of alkyl (meth)acrylate and at least one monomer of hydroxyalkyl (meth)acrylate.

In an embodiment of the presently claimed invention, the alkyl (meth)acrylate described hereinabove is selected from the group consisting of methyl (meth)acrylate, ethyl (meth)acrylate, propyl (meth)acrylate, isopropyl (meth)acrylate, butyl (meth)acrylate, isobutyl (meth)acrylate, hexyl (meth)acrylate, 2-ethylhexyl (meth)acrylate, nonyl (meth)acrylate, lauryl (meth)acrylate, stearyl (meth)acrylate and isodecyl (meth)acrylate. In a preferred embodiment of the presently claimed invention, the alkyl (meth)acrylate described hereinabove is selected from the group consisting of methyl (meth)acrylate, ethyl (meth)acrylate, propyl (meth)acrylate, isopropyl (meth)acrylate, butyl (meth)acrylate and isobutyl (meth)acrylate.

In an embodiment of the presently claimed invention, the hydroxyalkyl (meth)acrylate described hereinabove is selected from the group consisting of 2-hydroxyethyl (meth)acrylate, 2-hydroxypropyl (meth)acrylate and 2-hydroxybutyl (meth)acrylate.

In an embodiment of the presently claimed invention, the polyethylene glycol alkyl ether (meth)acrylate is selected from the group consisting of polyethylene glycol methylether acrylate, polyethylene glycol ethyl ether acrylate, polyethylene glycol propyl ether acrylate and polyethylene glycol butyl ether acrylate.

In an embodiment of the presently claimed invention, the linear di-block polymer has a number average molecular weight ($M_n$) in the range of from ≥1000 g/mol to ≤25000 g/mol, determined according to gel permeation chromatography against a polystyrene standard. In a preferred embodiment of the presently claimed invention, the polymeric pigment dispersant has a number average molecular weight ($M_n$) in the range of from ≥1000 g/mol to ≤15000 g/mol.

In an embodiment of the presently claimed invention, the linear di-block has a polydispersity in the range of from ≥1.2 to ≤20, determined according to gel permeation chromatography against a polystyrene standard. In another embodiment of the presently claimed invention, the linear di-block has a polydispersity in the range of from ≥1.2 to ≤10, determined according to gel permeation chromatography against a polystyrene standard. In a preferred embodiment of the presently claimed invention, the polymeric pigment dispersant has a polydispersity in the range of from ≥1.2 to ≤3.5, determined according to gel permeation chromatography against a polystyrene standard. In a most preferred embodiment of the presently claimed invention, the polymeric pigment dispersant has a polydispersity in the range of from ≥1.2 to ≤2.2, determined according to gel permeation chromatography against a polystyrene standard.

In an embodiment of the presently claimed invention, the polymer backbone (P) described hereinabove is a block polymer with at least two blocks.

Random Polymer

In an embodiment of the presently claimed invention, the polymer backbone (P) described hereinabove is a random polymer.

In a yet another embodiment of the presently claimed invention, the random polymer is obtained by a free radical polymerization.

In an embodiment of the presently claimed invention, the random polymer is obtained by free radical polymerization referred to as atom transfer radical polymerization (ATRP).

The ATRP process is described to provide highly uniform products having controlled structure and is also referred to as controlled radical polymerization (CRP). The ATRP process is described for preparation of copolymers which are useful in a wide variety of applications, including pigment dispersant in U.S. Pat. Nos. 6,365,666 B1 and 6,642,301 B2.

The ATRP process description can be found in detail in U.S. Pat. Nos. 5,807,937 A, 5,763,548 A, 5,789,487 A and WO 1998/40415 A1.

For the purposes of the presently claimed invention, the random polymer can be obtained by other polymerization techniques like reversible addition-fragmentation chain transfer (RAFT), ring-opening metathesis polymerization (ROMP), and anionic and cationic polymerizations.

In an embodiment of the presently claimed invention, the random polymer is obtained by reacting a mixture ($M_n$) comprising:
(a) glycidyl methacrylate and/or glycidyl acrylate;
(b) at least one monomer selected from the group consisting of alkyl (meth)acrylate, hydroxyalkyl (meth)acrylate and cycloalkyl (meth)acrylate;
(c) optionally at least one monomer of styrene; and
(d) optionally at least one monomer selected from the group consisting of vinyl monomers, monoethylenically unsaturated monomers bearing urea or keto groups and benzyl (meth)acrylate, optionally in the presence of at least one solvent (S2).

In a preferred embodiment of the presently claimed invention, the random polymer is obtained by reacting a mixture ($M_n$) comprising:
(a) glycidyl methacrylate and/or glycidyl acrylate; and
(b) at least one monomer selected from the group consisting of alkyl (meth)acrylate, hydroxyalkyl (meth)acrylate and cycloalkyl (meth)acrylate;

In a preferred embodiment of the presently claimed invention, the random polymer is obtained by reacting a mixture ($M_n$) comprising:
(a) glycidyl methacrylate and/or glycidyl acrylate;
(b) at least one monomer selected from the group consisting of alkyl (meth)acrylate, hydroxyalkyl (meth)acrylate and cycloalkyl (meth)acrylate; and
(c) at least one monomer of styrene.

In an embodiment of the presently claimed invention, the random polymer is obtained by reacting a mixture ($M_n$) comprising:
(a) glycidyl methacrylate and/or glycidyl acrylate;
(b) at least one monomer selected from the group consisting of alkyl (meth)acrylate, hydroxyalkyl (meth)acrylate and cycloalkyl (meth)acrylate;
(c) at least one monomer of styrene; and
(d) at least one monomer selected from the group consisting of vinyl monomers, monoethylenically unsaturated monomers bearing urea or keto groups and benzyl (meth)acrylate, In a preferred embodiment of the presently claimed invention, the random polymer is obtained by reacting a mixture ($M_n$) comprising:
(a) glycidyl methacrylate and/or glycidyl acrylate;
(b) at least one monomer selected from the group consisting of alkyl (meth)acrylate, hydroxyalkyl (meth)acrylate and cycloalkyl (meth)acrylate; and
(c) at least one monomer of styrene.
in the presence of at least one solvent (S2).

In a preferred embodiment of the presently claimed invention, the random polymer is obtained by reacting a mixture ($M_n$) comprising:
(a) glycidyl methacrylate and/or glycidyl acrylate; and
(b) at least one monomer selected from the group consisting of alkyl (meth)acrylate, hydroxyalkyl (meth)acrylate and cycloalkyl (meth)acrylate;
in the presence of at least one solvent (S2).

In an embodiment of the presently claimed invention, the alkyl (meth)acrylate described hereinabove is selected from the group consisting of methyl (meth)acrylate, ethyl (meth) acrylate, propyl (meth)acrylate, isopropyl (meth)acrylate, butyl (meth)acrylate, isobutyl (meth)acrylate, hexyl (meth) acrylate, 2-ethylhexyl (meth)acrylate, nonyl (meth)acrylate, lauryl (meth)acrylate, stearyl (meth)acrylate and isodecyl (meth)acrylate). In a preferred embodiment of the presently claimed invention, the alkyl (meth)acrylate described hereinabove is selected from the group consisting of methyl (meth)acrylate, ethyl (meth)acrylate, propyl (meth)acrylate, isopropyl (meth)acrylate, butyl (meth)acrylate and isobutyl (meth)acrylate.

In an embodiment of the presently claimed invention, the hydroxyalkyl (meth)acrylate described hereinabove is selected from the group consisting of 2-hydroxyethyl (meth) acrylate, 2-hydroxypropyl (meth)acrylate and 2-hydroxybutyl (meth)acrylate.

In an embodiment of the presently claimed invention, the cycloalkyl (meth)acrylate described hereinabove is selected from the group consisting of cyclopentyl (meth)acrylate, cyclohexyl(meth)acrylate, dicyclopentadiene (meth)acrylate, dicyclopentanyl (meth)acrylate, tricyclodecanyl (meth) acrylate, isobornyl (meth)acrylate, 4-tert-butylcyclohexyl (meth)acrylate, norbornyl (meth)acrylate and bornyl (meth) acrylate.

In an embodiment of the presently claimed invention, the at least one monomer of styrene described hereinabove is selected from the group consisting of 4-methyl styrene, 3-methyl styrene, 4-tert-butyl styrene, 4-tert-butoxy styrene, 2-bromostyrene, 3-bromostyrene, 4-bromostyrene, 2-chlorostyrene, 3-chlorostyrene, 4-chlorostyrene, 4-chloro-ε-methylstyrene, 2,6-dichloro styrene, 2-flurostyrene, 3-flurostyrene, 4-fluorostyrene, 2,6-difluorostyrene, 3-nitrostyrene and 4-acetoxy styrene.

In an embodiment of the presently claimed invention, the at least one vinyl monomer described hereinabove is selected from the group consisting of 3-vinyl benzoic acid, 4-vinyl benzoic acid and 4-vinylbenzyl chloride.

In an embodiment of the presently claimed invention, the monoethylenically unsaturated monomer bearing urea or keto groups described hereinabove is selected from the group consisting of 2-(2-oxo-imidazolidin-1-yl)ethyl (meth) acrylate, 2-ureido (meth)acrylate, N-[2-(2-oxooxazolidin-3-yl)ethyl]methacrylate, acetoacetoxyethyl acrylate, acetoacetoxypropyl methacrylate, acetoacetoxybutyl methacrylate, 2-(acetoacetoxy)ethyl methacrylate, diacetoneacrylamide (DAAM), diacetonemethacrylamide, N-(beta-ureido ethyl) acrylamide and N-(beta-ureido ethyl) methacrylamide.

In an embodiment of the presently claimed invention, the solvent (S2) is selected from the group consisting of xylene, toluene, methanol, ethanol, n-propanol, isopropanol, butanol, butoxyethanol, acetone, butanone, pentanone, hexanone, methyl isobutyl ketone, ethyl acetate, butyl acetate, amyl acetate, methoxy propyl acetate, tetrahydrofuran, diethyl ether, ethylene glycol, polyethylene glycol and mixtures thereof. In a preferred embodiment of the presently claimed invention, the solvent (S2) is selected from the group consisting of toluene, n-propanol, isopropanol, methyl isobutyl ketone and mixtures thereof.

In an embodiment of the presently claimed invention, the random polymer has a number average molecular weight ($M_n$) in the range of from ≥1000 g/mol to ≤25000 g/mol, determined according to gel permeation chromatography against a polystyrene standard. In a preferred embodiment of the presently claimed invention, the polymeric pigment dispersant has a number average molecular weight ($M_n$) in the range of from ≥1000 g/mol to ≤15000 g/mol.

In an embodiment of the presently claimed invention, the random polymer has a polydispersity in the range of from ≥1.5 to ≤20, determined according to gel permeation chromatography against a polystyrene standard. In another embodiment of the presently claimed invention, the random polymer has a polydispersity in the range of from ≥1.5 to ≤10, determined according to gel permeation chromatography against a polystyrene standard. In a preferred embodiment of the presently claimed invention, the polymeric pigment dispersant has a polydispersity in the range of from ≥1.5 to ≤5, determined according to gel permeation chromatography against a polystyrene standard. In a most preferred embodiment of the presently claimed invention, the polymeric pigment dispersant has a polydispersity in the range of from ≥1.5 to ≤3, determined according to gel permeation chromatography against a polystyrene standard.

Graft Polymer

In an embodiment of the presently claimed invention, the polymeric pigment dispersant described hereinabove is a graft polymer.

In an embodiment of the presently claimed invention, the graft polymer described hereinabove and hereinbelow comprises at least one polyester block.

In a yet another embodiment of the presently claimed invention, the polyester block described hereinabove is obtained from monomeric units of a hydroxy-functional aliphatic acid or a hydroxy-functional aromatic acid or hydroxy-functional araliphatic acid. In a preferred embodiment of the presently claimed invention, the polyester block described hereinabove is obtained from monomeric units of a hydroxy-functional aliphatic acid. In an embodiment of the presently claimed invention, the hydroxy-functional aliphatic acid described hereinabove is selected from the group consisting of glycolic acid, lactic acid, 5-hydroxy valeric acid, 3-hydroxy-butyric acid, 4-hydroxy-valeric acid, 12-hydroxy stearic acid and 6-hydroxy caproic acid.

In a preferred embodiment of the presently claimed invention, the polyester block described hereinabove is obtained in the presence of a saturated fatty acid or an unsaturated fatty acid.

Representative examples of saturated or the unsaturated fatty acid is selected preferably from the group consisting of oleic acid, linolenic acid, palmitoleic acid and tall oil fatty acid.

In another embodiment of the presently claimed invention, the polyester block described hereinabove is obtained from monomeric units of a lactone. In a yet another embodiment of the presently claimed invention, the lactone described hereinabove is selected from the group consisting of δ-valerolactone, ε-caprolactone, β-methyl-δ-valerolactone, 2-methyl-ε-caprolactone, 3-methyl-ε-caprolactone, 4-methyl-ε-caprolactone, 5-ter-butyl-ε-caprolactone, 7-methyl-ε-caprolactone, 4,4,6-trimethyl-ε-caprolactone and β-propiolactone.

In an embodiment of the presently claimed invention, the total weight of the at least one polyester block described hereinabove is in the range of from ≥5 wt. % to ≤95 wt. %, based on the total weight of the polymeric pigment dispersant. In a preferred embodiment of the presently claimed invention, the total weight of the at least one polyester block described hereinabove is in the range of from ≥45 wt. % to ≤95 wt. %, based on the total weight of the polymeric pigment dispersant. In a most preferred embodiment of the presently claimed invention, the total weight of the at least one polyester block described hereinabove is in the range of from ≥45 wt. % to ≤80 wt. %, based on the total weight of the polymeric pigment dispersant In an embodiment of the presently claimed invention, the polyester block described hereinabove is bonded to the moiety of the formula (I) and/or the polymer backbone (P) via a —C(=O)—O— group.

In another embodiment of the presently claimed invention, the graft polymer described hereinabove and hereinbelow comprises at least one polyether block.

In another embodiment of the presently claimed invention, the at least one polyether block described hereinabove comprises a polyoxyethylene group comprising from 10 to 120 ethylene oxide units. In a preferred embodiment of the presently claimed invention, the at least one polyether block described hereinabove comprises a polyoxyethylene group comprising from 20 to 60 ethylene oxide units.

In an embodiment of the presently claimed invention, the polyether block described hereinabove is bonded to the moiety of the formula (I) and/or the polymer backbone (P) via a —C(=O)—O— group.

An aspect of the presently claimed invention is directed to a process for the preparation of at least one polymeric pigment dispersant comprising a linear di-block polymer backbone comprising at least the steps of:

reacting a di-block polymer as described hereinabove with a compound of the formula (IV):

wherein

R1 is selected from the group consisting of unsubstituted or substituted naphthyl, unsubstituted or substituted anthracenyl and unsubstituted or substituted phenanthrenyl;

R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;

R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—OH group;

at a temperature from ≥80° C. to ≤150° C.; and wherein the linear di-block polymer comprises a first and a second block and is obtained by a living free radical polymerization described hereinabove, optionally in the presence of a solvent (S3).

In an embodiment of the presently claimed invention, the solvent (S3) is selected from the group consisting of butyl acetate, methyl N-amyl ketone, methyl isoamyl ketone and isopropanol.

In an embodiment, the presently claimed invention is directed to a process for the preparation of at least one polymeric pigment dispersant comprising a linear di-block polymer backbone comprising at least the steps of:

reacting a di-block polymer as described hereinabove with a compound of the formula (IV):

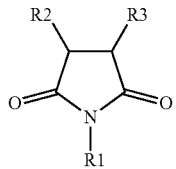

wherein
R1 is selected from the group consisting of naphthyl, anthracenyl and phenanthrenyl which are each unsubstituted or substituted with 1, 2 or 3 —OH; and
R2 and R3 together with the carbon atoms to which they are bonded form a ring selected from the group consisting of phenyl and cyclohexyl which are each substituted with one —C(=O)—OH group;
at a temperature from ≥100° C. to ≤130° C.; and
wherein the linear di-block polymer comprises a first and a second block and is obtained by a living free radical polymerization described hereinabove, optionally in the presence of a solvent (S3).

In a preferred embodiment, the presently claimed invention is directed to a process for the preparation of at least one polymeric pigment dispersant comprising a linear di-block polymer backbone comprising at least the steps of:
reacting a di-block polymer as described hereinabove with a compound of the formula (IV):

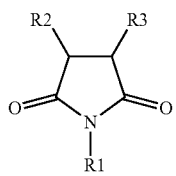

wherein
R1 is naphthyl, which is unsubstituted or substituted with 1, 2 or 3 —OH; and
R2 and R3 together with the carbon atoms to which they are bonded form a ring selected from the group consisting of phenyl and cyclohexyl which are each substituted with one —C(=O)—OH group;
at a temperature from ≥100° C. to ≤130° C.; and
wherein the linear di-block polymer comprises a first and a second block and is obtained by a living free radical polymerization described hereinabove, optionally in the presence of a solvent (S3).

An aspect of the presently claimed invention is directed to a process for the preparation of at least one polymeric pigment dispersant comprising a random polymer comprising at least the steps of:
(a) reacting a random polymer as described hereinabove with a compound of the formula (IV):

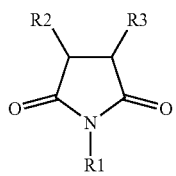

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—OH group; and
(b) reacting the compound obtained in step (a) with at least one monomer of a lactone at a temperature from ≥30° C. to ≤190° C.

In an embodiment, the presently claimed invention is directed to a process for the preparation of at least one polymeric pigment dispersant comprising a random polymer comprising at least the steps of:
(a) reacting a random polymer as described hereinabove with a compound of the formula (IV):

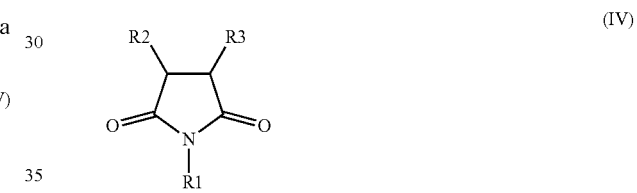

wherein
R1 is selected from the group consisting of naphthyl, anthracenyl and phenanthrenyl which are each unsubstituted or substituted with 1, 2 or 3 —OH; and
R2 and R3 together with the carbon atoms to which they are bonded form a ring selected from the group consisting of phenyl and cyclohexyl which are each substituted with one —C(=O)—OH group; and
(b) reacting the compound obtained in step (a) with at least one monomer of a lactone at a temperature from ≥100° C. to ≤140° C.

In a preferred embodiment, the presently claimed invention is directed to a process for the preparation of at least one polymeric pigment dispersant comprising a random polymer comprising at least the steps of:
(a) reacting a random polymer as described hereinabove with a compound of the formula (IV):

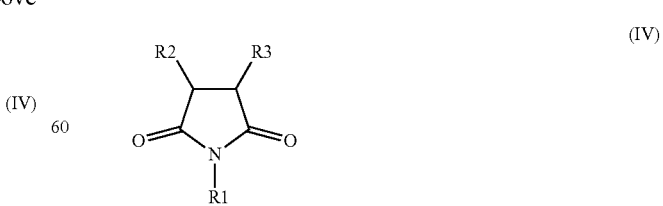

wherein
R1 is naphthyl, which is unsubstituted or substituted with 1, 2 or 3 —OH; and R2 and R3 together with the carbon atoms to which they are bonded form a ring selected from the group consisting of phenyl and cyclohexyl which are each substituted with one —C(=O)—OH group; and (b) reacting the compound obtained in step (a) with at least one monomer of a lactone at a temperature from ≥100° C. to ≤140° C.

In an embodiment of the presently claimed invention, the at least one monomer of a lactone described hereinabove is selected from the group consisting of δ-valerolactone, ε-caprolactone, β-methyl-δ-valerolactone, 2-methyl-ε-caprolactone, 3-methyl-ε-caprolactone, 4-methyl-ε-caprolactone, 5-ter-butyl-ε-caprolactone, 7-methyl-ε-caprolactone, 4,4,6-trimethyl-ε-caprolactone and β-propiolactone.

An aspect of the presently claimed invention is directed to a process for the preparation of at least one polymeric pigment dispersant comprising a random polymer comprising at least the steps of:

(a) reacting at least one polyalkylene glycol monoalkyl ether and at least one carboxylic acid anhydride at a temperature in the range from ≥70° C. to ≤140° C. to obtain a mixture; and (b) reacting the mixture obtained in step (a) with a random polymer described hereinabove and a compound of the formula (IV):

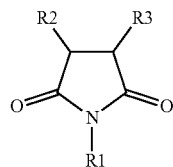

(IV)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—OH group;
at a temperature in the range from ≥70° C. to ≤140° C.

In an embodiment, the presently claimed invention is directed to a process for the preparation of at least one polymeric pigment dispersant comprising a random polymer comprising at least the steps of:
(a) reacting at least one polyalkylene glycol monoalkyl ether and at least one carboxylic acid anhydride at a temperature in the range from ≥100° C. to ≤140° C. to obtain a mixture; and
(b) reacting the mixture obtained in step (a) with a random polymer described hereinabove and a compound of the formula (IV):

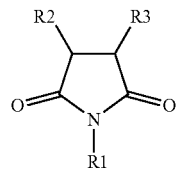

(IV)

wherein
R1 is selected from the group consisting of naphthyl, anthracenyl and phenanthrenyl which are each unsubstituted or substituted with 1, 2 or 3 —OH; and
R2 and R3 together with the carbon atoms to which they are bonded form a ring selected from the group consisting of phenyl and cyclohexyl which are each substituted with one —C(=O)—OH group;
at a temperature in the range from ≥100° C. to ≤140° C.

In a preferred embodiment, the presently claimed invention is directed to a process for the preparation of at least one polymeric pigment dispersant comprising a random polymer comprising at least the steps of:
(a) reacting at least one polyalkylene glycol monoalkyl ether and at least one carboxylic acid anhydride at a temperature in the range from ≥100° C. to ≤140° C. to obtain a mixture; and
(b) reacting the mixture obtained in step (a) with a random polymer described hereinabove and a compound of the formula (IV):

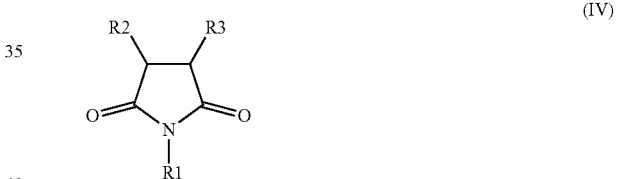

(IV)

wherein
R1 is naphthyl, which is unsubstituted or substituted with 1, 2 or 3 —OH; and
R2 and R3 together with the carbon atoms to which they are bonded form a ring selected from the group consisting of phenyl and cyclohexyl which are each substituted with one —C(=O)—OH group;
at a temperature in the range from ≥100° C. to ≤140° C.

Another aspect of the presently claimed invention is directed to a pigment dispersion comprising at least one polymeric pigment dispersant according to the presently claimed invention, at least one solvent (S5) and at least one pigment.

For the purposes of the presently claimed invention, the at least one solvent (S5) is selected from the group consisting of organic solvents. Representative examples of classes of organic solvents include, but are not limited to, alcohols, ketones or ketoalcohols, ethers, esters and polyhydric alcohols. Representative examples of organic solvents include, but are not limited to, xylene, toluene, methanol, ethanol, n-propanol, isopropanol, acetone, methyl ethyl ketone, dimethyl ether, methyl ethyl ether, ethyl acetate, ethyl lactate, ethylene glycol, diethylene glycol and butyl-2-hydroxyethyl ether.

For the purposes of the presently claimed invention, the at least one pigment is a virtually insoluble, finely dispersed, organic or inorganic colorant as per the definition in the German standard specification DIN 55944.

Representative examples of organic pigments include but are not limited to, monoazo pigments, such as C.I. Pigment Brown 25; C.I. Pigment Orange 5, 13, 36 and 67; C.I. Pigment Red 1, 2, 3, 5, 8, 9, 12, 17, 22, 23, 31, 48:1, 48:2, 48:3, 48:4, 49, 49:1, 52:1, 52:2, 53, 53:1, 53:3, 57:1, 63, 112, 146, 170, 184, 210, 245 and 251; C.I. Pigment Yellow 1, 3, 73, 74, 65, 97, 151 and 183;
disazo pigments, such as C.I. Pigment Orange 16, 34 and 44; C.I. Pigment Red 144, 166, 214 and 242; C.I. Pigment Yellow 12, 13, 14, 16, 17, 81, 83, 106, 113, 126, 127, 155, 174, 176 and 188; anthanthrone pigments, such as C.I. Pigment Red 168 (C.I. Vat Orange 3); anthraquinone pigments, such as C.I. Pigment Yellow 147 and 177; C.I. Pigment Violet 31; anthraquinone pigments, such as C.I. Pigment Yellow 147 and 177; C.I. Pigment Violet 31; anthrapyrimidine pigments: C.I. Pigment Yellow 108 (C.I. Vat Yellow 20); quinacridone pigments, such as C.I. Pigment Red 122, 202 and 206; C.I. Pigment Violet 19; quinophthalone pigments, such as C.I. Pigment Yellow 138; dioxazine pigments, such as C.I. Pigment Violet 23 and 37;
flavanthrone pigments, such as C.I. Pigment Yellow 24 (C.I. Vat Yellow 1); indanthrone pigments, such as C.I. Pigment Blue 60 (C.I. Vat Blue 4) and 64 (C.I. Vat Blue 6); isoindoline pigments, such as C.I. Pigment Orange 69; C.I. Pigment Red 260; C.I. Pigment Yellow 139 and 185; isoindolinone pigments, such as C.I. Pigment Orange 61; C.I. Pigment Red 257 and 260; C.I. Pigment Yellow 109, 110, 173 and 185; isoviolanthrone pigments, such as C.I. Pigment Violet 31 (C.I. Vat Violet 1); metal complex pigments, such as C.I. Pigment Yellow 117, 150 and 153; C.I. Pigment Green 8; perinone pigments, such as C.I. Pigment Orange 43 (C.I. Vat Orange 7); C.I. Pigment Red 194 (C.I. Vat Red 15); perylene pigments, such as C.I. Pigment Black 31 and 32; C.I. Pigment Red 123, 149, 178, 179 (C.I. Vat Red 23), 190 (C.I. Vat Red 29) and 224; C.I. Pigment Violet 29; phthalocyanine pigments, such as C.I. Pigment Blue 15, 15:1, 15:2, 15:3, 15:4, 15:6 and 16; C.I. Pigment Green 7 and 36; pyranthrone pigments, such as C.I. Pigment Orange 51; C.I. Pigment Red 216 (C.I. Vat Orange 4); thioindigo pigments, such as C.I. Pigment Red 88 and 181 (C.I. Vat Red 1); C.I. Pigment Violet 38 (C.I. Vat Violet 3); triarylcarbonium pigments, such as C.I. Pigment Blue 1, 61 and 62; C.I. Pigment Green 1; C.I. Pigment Red 81, 81:1 and 169; C.I. Pigment Violet 1, 2, 3 and 27; C.I. Pigment Black 1 (aniline black); C.I. Pigment Yellow 101 (aldazine yellow), and C.I. Pigment Brown 22.

Representative examples of inorganic pigments include, but are not limited to, white pigments such as titanium dioxide (C.I. Pigment White 6), zinc white, pigment grade zinc oxide; zinc sulfide, lithopone; lead white; furthermore white fillers such as barium sulfate and CaCO3, black pigments, such as iron oxide black (C.I. Pigment Black 11), iron manganese black, spinel black (C.I. Pigment Black 27), carbon black (C.I. Pigment Black 7); colour pigments, such as chromium oxide, chromium oxide hydrate green; chrome green (C.I. Pigment Green 48); cobalt green (C.I. Pigment Green 50); ultramarine green; cobalt blue (C.I. Pigment Blue 28 und 36); ultramarine blue, iron blue (C.I. Pigment Blue 27), manganese blue, ultramarine violet, cobalt violet, manganese violet, iron oxide read (C.I. Pigment Red 101); cadmium sulfoselenide (C.I. Pigment Red 108); molybdate read (C.I. Pigment Red 104); ultramarine read, iron oxide brown, mixed brown, spinel- and Korundum phases (C.I. Pigment Brown 24, 29 und 31), chrome orange; iron oxide yellow (C.I. Pigment Yellow 42); nickel titanium yellow (C.I. Pigment Yellow 53; C.I. Pigment Yellow 157 und 164); chrome titanium yellow; cadmium sulfide und cadmium zinc sulfide (C.I. Pigment Yellow 37 und 35); Chrome yellow (C.I. Pigment Yellow 34), zinc yellow, alkaline earth metal chromates; Naples yellow; bismuth vanadate (C.I. Pigment Yellow 184); interference pigments, such as metallic effect pigments based on coated metal platelets, pearl luster pigments based on mica platelets coated with metal oxide, and liquid crystal pigments.

For the purposes of the presently claimed invention, the at least one pigment is selected from the group consisting of metallic pigments and effect pigments. Representative examples of effect pigments include but are not limited to red pearlescent mica, white pearlescent mica, green organic mica, yellow mica, blue base mica.

For the purposes of the presently claimed invention, the at least one pigment can also comprise mixtures of two or more different pigments.

For the purposes of the presently claimed invention, the at least one pigment is preferably selected from the group consisting of BASF Perrindo Maroon L3920, BASF Perrindo Maroon L 3990, Sun Chemical Perrindo Ma-roon 229-8801, Sun Chemical Perrindo Maroon 229-6438, Sun Chemical Perrindo Violet 29, Clariant Hostaperm Brown HFR01, Sun Chemical Palomar Blue 248-4816 and BASF Heliogen Blue 7081 D.

In an embodiment of the presently claimed invention, the weight ratio of the polymeric pigment dispersant to the at least one pigment is in the range of from ≥0.1:1 to ≤3:1.

In a preferred embodiment of the presently claimed invention, the weight ratio of the polymeric pigment dispersant to the at least one pigment is in the range of from ≥0.25:1 to ≤1.5:1.

For the purposes of the presently claimed invention, the average particle size of the pigment particles is in the range of ≥10 nanometres to ≤10 microns, preferably in the range of ≥10 nanometres to ≤5 microns, more preferably in the range of ≥10 nanometres to ≤1 micron in diameter.

For the purposes of the presently claimed invention, the pigment dispersion may be prepared by methods known to those of ordinary skill in the art. Representative examples of the methods for preparing pigment dispersions include, but are not limited to, the use of energy intensive mixing or grinding using ball mills or media mills.

Another aspect of the presently claimed invention is directed to a coating composition comprising a pigment dispersion according to the presently claimed invention and at least one binder.

For the purposes of the presently claimed invention, representative examples of binders include, but are not limited to, paints, fillers, and additives. The representative examples of additives include, but are not limited to, surfactants, light stabilizers, UV-absorbers, anti-foaming agents, dyes, plasticizers, levelling agents and anti-skinning agents. For the purposes of the presently claimed invention, the at least one binder is preferably selected from the group consisting of poly(meth)acrylates, polystyrenics, polyesters, alkyds, polysaccharides and polyurethanes.

In an embodiment of the presently claimed invention, the coating composition is a solventborne composition. For the purposes of the presently claimed invention, the solventborne coating composition is a composition that comprises an organic solvent.

Representative examples of organic solvents include, but are not limited to, xylene, toluene, methanol, ethanol, n-propanol, isopropanol, acetone, methyl ethyl ketone, dimethyl ether, methyl ethyl ether, ethyl acetate, ethyl lactate, ethylene glycol, diethylene glycol and butyl-2-hydroxyethyl ether.

In an embodiment of the presently claimed invention, the coating composition is a waterborne composition. For the purposes of the presently claimed invention, the waterborne coating composition is a composition that comprises water as a main solvent. However, 0 wt. % to ≤10 wt. %, preferably 0 wt. % to ≤5 wt. %, and most preferably 0 wt. % to ≤1 wt. % of organic solvents may be present in the waterborne coating compositions.

In an embodiment of the presently claimed invention, a clearcoat material comprises the coating composition described hereinabove.

In an embodiment of the presently claimed invention, a basecoat material comprises the coating composition described hereinabove.

An aspect of the presently claimed invention is directed to a use of a pigment dispersion according to the presently claimed invention in printing ink, automotive basecoat, automotive clearcoat, mill base, furniture coatings and wood coatings.

In an embodiment of the presently claimed invention, the pigment dispersion described hereinabove is used as a clearcoat material for industrial coatings selected from the group consisting of automotive OEM finishing, the finishing of parts for installation in or on automobiles and/or utility vehicles and automotive refinish, topcoat material, and electrodepositable coating material.

Another aspect of the presently claimed invention is directed to an article coated with at least one layer formed from the coating composition according to the presently claimed invention.

For the purposes of the presently claimed invention, the coating composition can preferably be applied to the article by any of the customary application methods. Representative examples of the application methods include, but are not limited to, spraying, knife coating, spreading, pouring dipping, impregnating, trickling or rolling. With respect to such application, the substrate to be coated may itself be at rest, with the application unit or equipment being moved. Alternatively, the substrate to be coated, more particularly a coil, may be moved, with the application unit being at rest relative to the substrate or being moved appropriately. Pref-erable application methods are air spraying, airless spraying, high speed rotation, electro-static spray application, alone or in conjunction with hot spray application such as hot air spraying, for example.

For the purposes of the presently claimed invention, the coating composition of the presently claimed invention can be applied to an uncoated or a precoated article.

An aspect of the presently claimed invention is directed to a compound of formula (IV)

(IV)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl which are each substituted with one —C(=O)—OH group;
whereby the following compound N-napthalenyl-4-carboxy-1,2-phthalimide is excluded.

Another aspect of the presently claimed invention is directed to a compound of formula (IV)

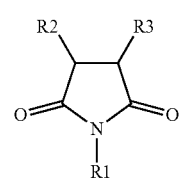

(IV)

wherein
R1 is selected from the group consisting of unsubstituted naphthyl or naphthyl substituted with 1, 2 or 3 —OH; and
R2 and R3 together with the carbon atoms to which they are bonded form a ring selected from the group consisting of phenyl and cyclohexyl which are each substituted with one —C(=O)—OH group.

For the purposes of the presently claimed invention, the compound of formula (IV) described hereinabove and hereinbelow is also referred to as anchoring group or anchor or anchor(s). For the purposes of the presently claimed invention, the polymeric pigment dispersant described hereinabove and hereinbelow is also referred to as pigment dispersant or hyperdispersant or polymeric dispersant or dispersant. It is an advantage of the presently claimed invention, that the compounds of formula (IV) of the presently claimed invention were surprisingly found to provide colloidal stabilization against aggregation and/or agglomeration of the particulate or particles when functioning as a dispersant. The compounds of formula (IV) as described hereinabove and hereinbelow provide good interaction and strong adsorption with a pigment surface by even weak interactions like π-π and hydrogen bonding interaction. Further, it is an advantage of the presently claimed invention that the polymeric dispersants can be prepared in a simple and efficient method that is cost effective. The compounds of formula (IV) as described hereinabove and hereinbelow have increased solubility in low polarity solvents that makes the synthesis of the polymeric pigment dispersant easier than the conventionally known methods. The polymeric pigment dispersants of the presently claimed invention provide high chroma and transparent colour in comparison to traditional hyperdispersants or pigment dispersants.

In a preferred embodiment, the presently claimed invention is directed to a polymeric pigment dispersant comprising a polymer backbone (P) and at least one moiety of the formula (I):

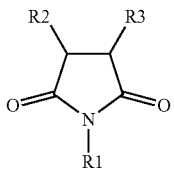

wherein
R1 is naphthyl, which is unsubstituted or substituted with 1, 2, 3, 4 or 5 substituents independently of each other selected from the group consisting of F, Cl, Br, I, —NO$_2$, —CN, —OH, —C$_1$-C$_6$-alkyl, —C(=O)—C$_1$-C$_6$-alkyl, —C(=O)—O—C$_1$-C$_6$-alkyl, —C(=O)—O— phenyl, —CH$_2$—C(=O)—C$_1$-C$_6$-alkyl, —C(=O)—NH(C$_1$-C$_6$)alkyl, —C(=O)—NH-phenyl, —C$_1$-C$_6$-alkyl; wherein —C$_1$-C$_6$-alkyl is itself unsubstituted or substituted with 1, 2, 3, 4 or 5 substituents independently of each other selected from the group consisting of F, Cl, Br, I, —CN, —OH, —O—CF$_3$, —O—CH$_3$ and —O—C$_2$H$_5$;
R2 and R3 together with the carbon atoms to which they are bonded form a ring selected from the group consisting of phenyl and cyclohexyl which are each substituted with one —C(=O)—O— group; and
whereby the moiety of the formula (I) is bonded to the polymer backbone (P) via the —C(=O)—O— group.

In a preferred embodiment, the presently claimed invention is directed to a polymeric pigment dispersant comprising a polymer backbone (P) and at least one moiety of the formula (I):

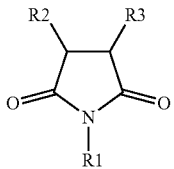

wherein
R1 is selected from the group consisting of naphthyl, anthracenyl and phenanthrenyl which are each unsubstituted or substituted with 1, 2 or 3 —OH;
R2 and R3 together with the carbon atoms to which they are bonded form a ring selected from the group consisting of phenyl and cyclohexyl which are each substituted with one —C(=O)—O— group; and
whereby the moiety of the formula (I) is bonded to the polymer backbone (P) via the —C(=O)—O— group.

In a preferred embodiment, the presently claimed invention is directed to a polymeric pigment dispersant comprising a polymer backbone (P) and at least one moiety of the formula (I):

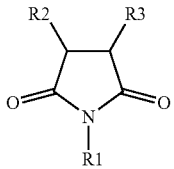

wherein
R1 is naphthyl which is unsubstituted or substituted with 1, 2 or 3 —OH;
R2 and R3 together with the carbon atoms to which they are bonded form a ring selected from the group consisting of phenyl and cyclohexyl which are each substituted with one —C(=O)—O— group; and
whereby the moiety of the formula (I) is bonded to the polymer backbone (P) via the —C(=O)—O— group.

In a preferred embodiment of the presently claimed invention, wherein the at least one moiety of the formula (I) is obtained by reacting at least one compound of formula (II)

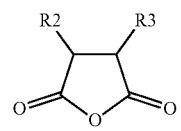

wherein
R2 and R3 together with the carbon atoms to which they are bonded form a substituted phenyl or a substituted C$_3$-C$_{10}$ cycloalkyl or a substituted C$_4$-C$_{10}$ cycloalkenyl which are each substituted with one —C(=O)—OH group;
with at least one compound of formula (III)

R1—NH$_2$  (III)

wherein
R1 is selected from the group consisting of unsubstituted or substituted naphthyl, unsubstituted or substituted anthracenyl and unsubstituted or substituted phenanthrenyl; in the presence of at least one solvent.

Embodiments

In the following, there is provided a list of embodiments to further illustrate the present disclosure without intending to limit the disclosure to the specific embodiments listed below.

1. A polymeric pigment dispersant comprising a polymer backbone (P) and a moiety of the formula (I):

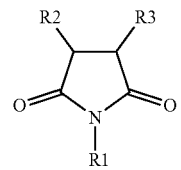

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted C$_1$-C$_{14}$ alkyl and a linear or a branched, substituted C$_2$-C$_{14}$ alkenyl, which are each substituted with one —C(=O)—O— group;
R3 is selected from the group consisting of a linear or a branched, substituted C$_1$-C$_{14}$ alkyl and a linear or branched, substituted C$_2$-C$_{14}$ alkenyl, which are each substituted with one —C(=O)—O— group; or R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—O— group; and whereby the moiety of the formula (I) is bonded to the polymer backbone (P) via the —C(=O)—O— group.

2. The polymeric pigment dispersant according to embodiment 1, wherein R1 is selected from the group consisting of naphthyl, anthracenyl and phenanthrenyl which are unsubstituted or substituted with 1, 2, 3, 4 or 5 substituents independently of each other selected from the group consisting of F, Cl, Br, I, —NO$_2$, —CN, —OH, —O—C$_1$-C$_6$-alkyl, —C(=O)—C$_1$-C$_6$-alkyl, —C(=O)—O—C$_1$-C$_6$-alkyl, —C(=O)—O-phenyl, —CH$_2$—C(=O)—C$_1$-C$_6$-alkyl, —C(=O)—NH(C$_1$-C$_6$)alkyl, —C(=O)—NH-phenyl, —C$_1$-C$_6$-alkyl; wherein —C$_1$-C$_6$-alkyl is itself unsubstituted or substituted with 1, 2, 3, 4 or 5 substituents independently of each other selected from the group consisting of F, Cl, Br, I, —CN, —OH, —O—CF$_3$, —O—CH$_3$ and —O—C$_2$H$_5$.

3. The polymeric pigment dispersant according to embodiment 1, wherein R1 is selected from the group consisting of naphthyl, anthracenyl and phenanthrenyl which are each unsubstituted or substituted with 1, 2 or 3 —OH.

4. The polymeric pigment dispersant according to embodiment 1, wherein R2 and R3 together with the carbon atoms to which they are bonded form a ring selected from the group consisting of phenyl and cyclohexyl which are each substituted with —C(=O)—O-group.

5. The polymeric pigment dispersant according to embodiment 1, wherein the at least one moiety of the formula (I) is obtained by reacting at least one compound of formula (II)

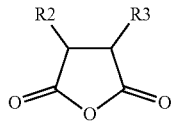

(II)

wherein

R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;

R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or R2 and R3 together with the carbon atoms to which they are bonded form a substituted phenyl or a substituted $C_3$-$C_{10}$ cycloalkyl or a substituted $C_4$-$C_{10}$ cycloalkenyl which are each substituted with one —C(=O)—OH group;

with at least one compound of formula (III)

R1—NH$_2$ (III)

wherein

R1 is selected from the group consisting of unsubstituted or substituted naphthyl, unsubstituted or substituted anthracenyl and unsubstituted or substituted phenanthrenyl;

optionally in the presence of at least one solvent.

6. The polymeric pigment dispersant according to embodiment 5, wherein the at least one compound of formula (II) is selected from the group consisting of phthalic anhydride, hexahydrophthalic anhydride, dodecenyl succinic anhydride, octadecenyl succinic anhydride, tetrahydrophthalic anhydride, methyltetrahydrophthalic anhydride and endomethylene tetrahydrophthalic anhydride, which are each substituted with at least one —C(=O)—OH group.

7. The polymeric pigment dispersant according to embodiment 5, wherein the at least one compound of formula (III) is selected from the group consisting of 1-naphthylamine and 7-hydroxy 1-naphthylamine.

8. The polymeric pigment dispersant according to embodiment 5, wherein the at least one solvent is a polar solvent having a boiling point in the range of ≥80° C. to ≤160° C. and a dielectric constant in the range of ≥11 to ≤30.

9. The polymeric pigment dispersant according to embodiment 8, wherein the at least one solvent is selected from the group consisting of methyl N-amyl ketone, ethyl methyl ketone, methyl isoamyl ketone and isopropanol.

10. The polymeric pigment dispersant according to embodiment 1, wherein the polymer backbone (P) is a linear di-block polymer.

11. The polymeric pigment dispersant according to embodiment 10, wherein the linear di-block polymer is obtained by a living free radical polymerization.

12. The polymeric pigment dispersant according to embodiment 10, wherein the linear di-block polymer has a formula A-B, wherein A is a first polymer block which is obtained by reacting a first mixture comprising at least one glycidyl (meth)acrylate; and B is a second polymer block which is obtained by reacting a second mixture comprising at least one monomer selected from the group consisting of alkyl (meth)acrylate, hydroxyalkyl (meth)acrylate, polyethylene glycol (meth)acrylate and polyethylene glycol alkyl ether (meth)acrylate.

13. The polymeric pigment dispersant according to embodiment 12, wherein the alkyl (meth)acrylate is selected from the group consisting of methyl (meth)acrylate, ethyl (meth)acrylate, propyl (meth)acrylate, isopropyl (meth)acrylate, butyl (meth)acrylate, isobutyl (meth)acrylate, hexyl (meth)acrylate, 2-ethylhexyl (meth)acrylate, nonyl (meth)acrylate, lauryl (meth)acrylate, stearyl (meth)acrylate and isodecyl (meth)acrylate.

14. The polymeric pigment dispersant according to embodiment 12, wherein the hydroxyalkyl (meth)acrylate is selected from the group consisting of 2-hydroxyethyl (meth)acrylate, 2-hydroxypropyl (meth)acrylate and 2-hydroxybutyl (meth)acrylate.

15. The polymeric pigment dispersant according to embodiment 12, wherein the polyethylene glycol alkyl ether (meth)acrylate is selected from the group consisting of polyethylene glycol methylether acrylate, polyethylene glycol ethyl ether acrylate, polyethylene glycol propyl ether acrylate and polyethylene glycol butyl ether acrylate.

16. The polymeric pigment dispersant according to embodiment 1, wherein the polymeric pigment dispersant has a number average molecular weight ($M_n$) in the range of from ≥1000 g/mol to ≤25000 g/mol, determined according to gel permeation chromatography against a polystyrene standard.

17. The polymeric pigment dispersant according to embodiment 1, wherein the polymeric pigment dispersant has a polydispersity in the range of from ≥1.2 to ≤20, determined according to gel permeation chromatography against a polystyrene standard.

18. The polymeric pigment dispersant according to embodiment 1, wherein the total weight of the at least one moiety of formula (I) is in the range of from ≥5 wt. % to ≤50 wt. %, based on the total weight of the polymeric pigment dispersant.

19. The polymeric pigment dispersant according to embodiment 1, wherein the polymer backbone (P) is a random polymer.

20. The polymeric pigment dispersant according to embodiment 19, wherein the random polymer is obtained by free radical polymerization.

21. The polymeric pigment dispersant according to embodiment 19, wherein the random polymer is obtained by reacting a mixture ($M_n$) comprising:
  (a) glycidyl methacrylate and/or glycidyl acrylate;
  (b) at least one monomer selected from the group consisting of alkyl (meth)acrylate, hydroxyalkyl (meth)acrylate and cycloalkyl (meth)acrylate;
  (c) optionally at least one monomer of styrene; and
  (d) optionally at least one monomer selected from the group consisting of vinyl monomers, monoethylenically unsaturated monomers bearing urea or keto groups and benzyl (meth)acrylate,
  optionally in the presence of at least one solvent.

22. The polymeric pigment dispersant according to embodiment 21, wherein the alkyl (meth)acrylate is selected from the group consisting of methyl (meth)acrylate, ethyl (meth)acrylate, propyl (meth)acrylate, isopropyl (meth)acrylate, butyl (meth)acrylate, isobutyl (meth)acrylate, hexyl (meth)acrylate, 2-ethylhexyl (meth)acrylate, nonyl (meth)acrylate, lauryl (meth)acrylate, stearyl (meth)acrylate and isodecyl (meth)acrylate).

23. The polymeric pigment dispersant according to embodiment 21, wherein the hydroxyalkyl (meth)acrylate is selected from the group consisting of 2-hydroxyethyl (meth)acrylate, 2-hydroxypropyl (meth)acrylate and 2-hydroxybutyl (meth)acrylate.

24. The polymeric pigment dispersant according to embodiment 21, wherein the cycloalkyl (meth)acrylate is selected from the group consisting of cyclopentyl (meth)acrylate, cy-clohexyl(meth)acrylate, dicyclopentadiene (meth)acrylate, dicyclopentanyl (meth)acrylate, tricyclodecanyl (meth)acrylate, isobornyl (meth)acrylate, 4-tert-butylcy-clohexyl (meth)acrylate, norbornyl (meth)acrylate and bornyl (meth)acrylate.

25. The polymeric pigment dispersant according to embodiment 21, wherein the at least one monomer of styrene is selected from the group consisting of 4-methyl styrene, 3-methyl styrene, 4-tert-butyl styrene, 4-tert-butoxy styrene, 2-bromostyrene, 3-bromostyrene, 4-bromostyrene, 2-chlorostyrene, 3-chlorostyrene, 4-chlorostyrene, 4-chloro-α-methylstyrene, 2,6-dichloro styrene, 2-fluro-styrene, 3-fluorstyrene, 4-fluorostyrene, 2,6-difluorosty-rene, 3-nitrostyrene and 4-acetoxy styrene.

26. The polymeric pigment dispersant according to embodiment 21, wherein the at least one vinyl monomer is selected from the group consisting of 3-vinyl benzoic acid, 4-vinyl benzoic acid and 4-vinylbenzyl chloride.

27. The polymeric pigment dispersant according to embodiment 21, wherein the monoethylenically unsaturated monomer bearing urea or keto groups is selected from the group consisting of 2-(2-oxo-imidazolidin-1-yl)ethyl (meth)acrylate, 2-ureido (meth)acrylate, N-[2-(2-oxooxa-zolidin-3-yl)ethyl]methacrylate, acetoacetoxyethyl acrylate, acetoacetoxypropyl methacrylate, acetoacetoxybutyl methacrylate, 2-(aceto-acetoxy)ethyl methacrylate, diacetoneacrylamide (DAAM), diacetonemethacrylamide, N-(beta-ureido ethyl) acrylamide and N-(beta-ureido ethyl) methacrylamide.

28. The polymeric pigment dispersant according to embodiment 21, wherein the solvent is selected from the group consisting of methanol, ethanol, n-propanol, isopropanol, butanol, butoxyethanol, acetone, butanone, pentanone, hexanone, methyl isobutyl ketone, ethyl acetate, butyl acetate, amyl acetate, methoxy propyl acetate, tetrahydrofuran, diethyl ether, ethylene glycol, polyethylene glycol and mixtures thereof.

29. The polymeric pigment dispersant according to embodiment 19, wherein the random copolymer has a number average molecular weight ($M_n$) in the range of from ≥1000 g/mol to ≤25000 g/mol, determined according to gel permeation chromatography against a polystyrene standard.

30. The polymeric pigment dispersant according to embodiment 19, wherein the random copolymer has a polydispersity in the range of from ≥1.5 to 20, determined according to gel permeation chromatography against a polystyrene standard.

31. The polymeric pigment dispersant according to embodiment 19, wherein the polymeric pigment dispersant is a graft polymer.

32. The polymeric pigment dispersant according to embodiment 31, wherein the graft polymer comprises at least one polyester block.

33. The polymeric pigment dispersant according to embodiment 32, wherein the polyester block is obtained from monomeric units of a hydroxy-functional aliphatic acid or a hy-droxy-functional aromatic acid or a hydroxy-functional araliphatic acid.

34. The polymeric pigment dispersant according to embodiment 32, wherein the polyester block is obtained in the presence of a saturated fatty acid or an unsaturated fatty acid.

35. The polymeric pigment dispersant according to embodiment 34, wherein the saturated or the unsaturated fatty acid is selected from the group consisting of oleic acid, linolenic acid, palmitoleic acid and tall oil fatty acid.

36. The polymeric pigment dispersant according to embodiment 33, wherein the hydroxy-functional aliphatic acid is selected from the group consisting of glycolic acid, lactic acid, 5-hydroxy valeric acid, 3-hydroxy-butyric acid, 4-hydroxy-valeric acid, 12-hydroxy stearic acid and 6-hydroxy caproic acid.

37. The polymeric pigment dispersant according to embodiment 32, wherein the polyester block is obtained from monomeric units of a lactone.

38. The polymeric pigment dispersant according to embodiment 37, wherein the lactone is selected from the group consisting of δ-valerolactone, ε-caprolactone, β-methyl-δ-valerolactone, 2-methyl-ε-caprolactone, 3-methyl-ε-caprolactone, 4-methyl-ε-caprolactone, 5-ter-butyl-ε-caprolactone, 7-methyl-ε-caprolactone, 4,4,6-trimethyl-ε-caprolactone and β-propiolactone.

39. The polymeric pigment dispersant according to embodiment 32, wherein the total weight of the at least one polyester block is in the range of from ≥5 wt. % to ≤95 wt. %, based on the total weight of the polymeric pigment dispersant.

40. The polymeric pigment dispersant according to embodiment 32, wherein the polyester block is bonded to the moiety of the formula (I) and/or the polymer backbone (P) via a —C(=O)—O— group.

41. The polymeric pigment dispersant according to embodiment 31, wherein the graft polymer comprises at least one polyether block.
42. The polymeric dispersant according to embodiment 41, wherein the at least one polyether block comprises a polyoxyethylene group comprising from 10 to 120 ethylene oxide units.
43. The polymeric pigment dispersant according to embodiment 41 or 42, wherein the polyether block is bonded to the moiety of the formula (I) and/or the polymer backbone (P) via —C(=O)—O— group.
44. A process for the preparation of at least one polymeric pigment dispersant according to embodiments 10 to 18 comprising at least the steps of:
reacting a linear di-block polymer with a compound of the formula (IV):

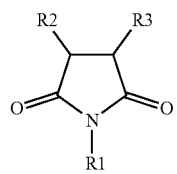

(IV)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—OH group;
at a temperature from ≥80° C. to ≤150° C.; and
wherein the linear di-block polymer comprises a first and a second block and is obtained by a living free radical polymerization, optionally in the presence of a solvent.
45. A process for the preparation of at least one polymeric pigment dispersant according to the embodiments 19 to 40 comprising at least the steps of:
(a) reacting a random polymer as defined in embodiments 19 to 21 with a compound of the formula (IV):

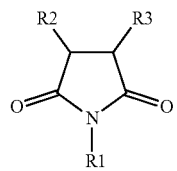

(IV)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—OH group;
and
(b) reacting the compound obtained in step (a) with at least one monomer of a lactone at a temperature from 30° C. to ≤190° C.
46. A process for the preparation of at least one polymeric pigment dispersant according to the embodiments 41 to 43 comprising at least the steps of:
(a) reacting at least one polyalkylene glycol monoalkyl ether and at least one carboxylic acid anhydride at a temperature in the range from ≥70° C. to ≤140° C. to obtain a mixture; and
(b) reacting the mixture obtained in step (a) with a random polymer as defined in embodiments 19 to 21 and a compound of the formula (IV):

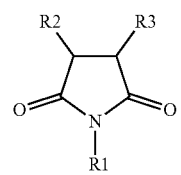

(IV)

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(=O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(=O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(=O)—OH group;
at a temperature in the range from ≥70° C. to ≤140° C.
47. A pigment dispersion comprising at least one polymeric pigment dispersant according to any one of the embodiments 1 to 43, at least one solvent and at least one pigment.
48. The pigment dispersion according to the embodiment 47, wherein the weight ratio of the polymeric pigment dispersant to the at least one pigment is in the range of from ≥0.1:1 to 3:1.
49. A coating composition comprising a pigment dispersion according to embodiment 47 or 48 and at least one binder.

50. The coating composition according to embodiment 49, wherein the coating composition is a solventborne composition.
51. The coating composition according to embodiment 49, wherein the coating composition is a waterborne composition.
52. The use of a pigment dispersion according to embodiment 47 or 48 in printing ink, automotive basecoat, automotive clearcoat, mill base, furniture coatings and wood coatings.
53. An article coated with at least one layer formed from the coating composition according to any one of the embodiments 49 to 51.
54. A compound of formula (IV)

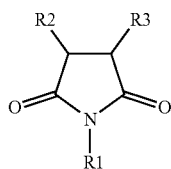

wherein
R1 is selected from the group consisting of unsubstituted or substituted naphthyl, unsubstituted or substituted anthracenyl and unsubstituted or substituted phenanthrenyl;
R2 is selected from the group consisting of a hydrogen; a linear or a branched, substituted $C_1$-$C_{14}$ alkyl and a linear or branched, substituted $C_2$-$C_{14}$ alkenyl, which are each substituted with one —C(═O)—OH group;
R3 is selected from the group consisting of a linear or a branched, substituted $C_1$-$C_{14}$ alkyl and a linear or branched, substituted $C_2$-$C_{14}$ alkenyl, which are each substituted with one —C(═O)—OH group; or
R2 and R3 together with the carbon atoms to which they are bonded form a substituted phenyl or a substituted $C_3$-$C_{10}$ cycloalkyl or a substituted $C_4$-$C_{10}$ cycloalkenyl which are each substituted with one —C(═O)—OH group;
whereby the following compound N-napthalenyl-4-carboxy-1,2-phthalimide is excluded.
55. A compound of formula (IV)

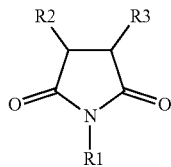

wherein
R1 is selected from the group consisting of unsubstituted naphthyl or naphthyl substituted with 1, 2 or 3 —OH; and
R2 and R3 together with the carbon atoms to which they are bonded form a ring selected from the group consisting of phenyl and cyclohexyl which are each substituted with one —C(═O)—OH group.

While the presently claimed invention has been described in terms of its specific embodiments, certain modifications and equivalents will be apparent to those skilled in the art and are intended to be included within the scope of the presently claimed invention Examples The presently claimed invention is illustrated in detail by non-restrictive working examples which follow. More particularly, the test methods specified hereinafter are part of the general disclosure of the application and are not restricted to the specific working examples.

Preparation of the Compounds of Formula (IV)

The preparation of the compounds of formula (IV) was carried out by reacting the anhydrides with an amine in a suitable solvent under reflux condition, followed by precipitation or vacuum drying under reduced pressure (Scheme 1: a to g).

Synthesis of the Compounds of Formula (IV) (Anchors C to F) is Shown Below in Scheme 1: a-g Scheme 1: a to g

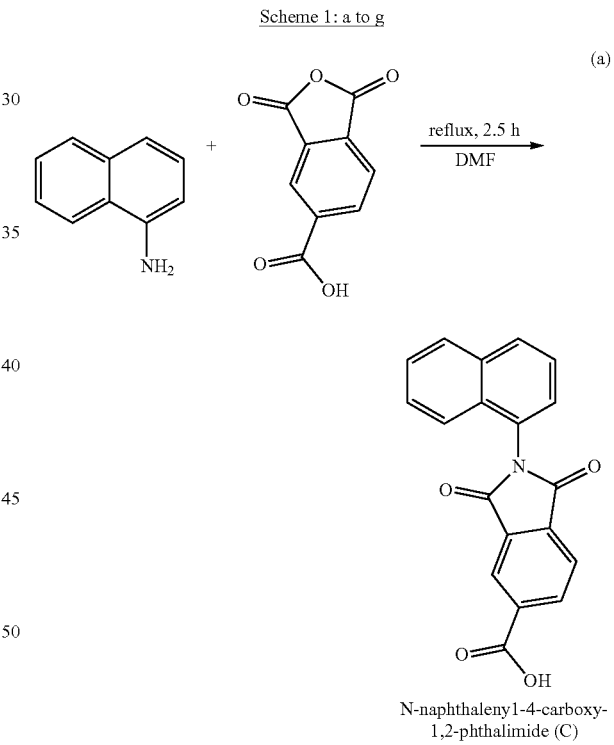

N-naphthaleny1-4-carboxy-1,2-phthalimide (C)

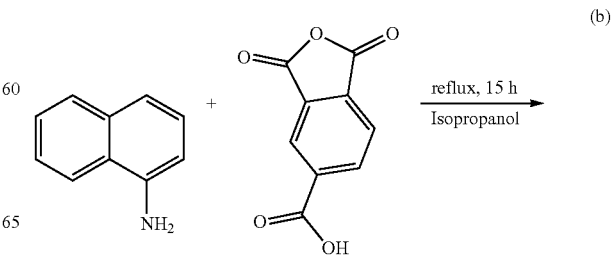

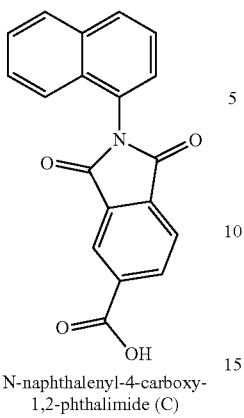
N-naphthalenyl-4-carboxy-
1,2-phthalimide (C)
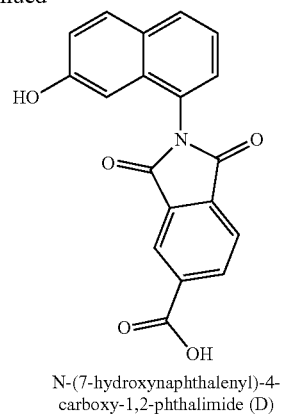
N-(7-hydroxynaphthalenyl)-4-
carboxy-1,2-phthalimide (D)
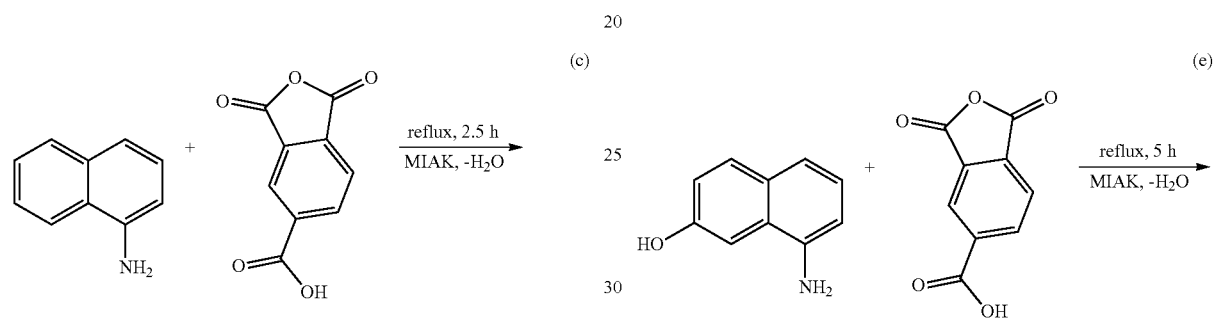
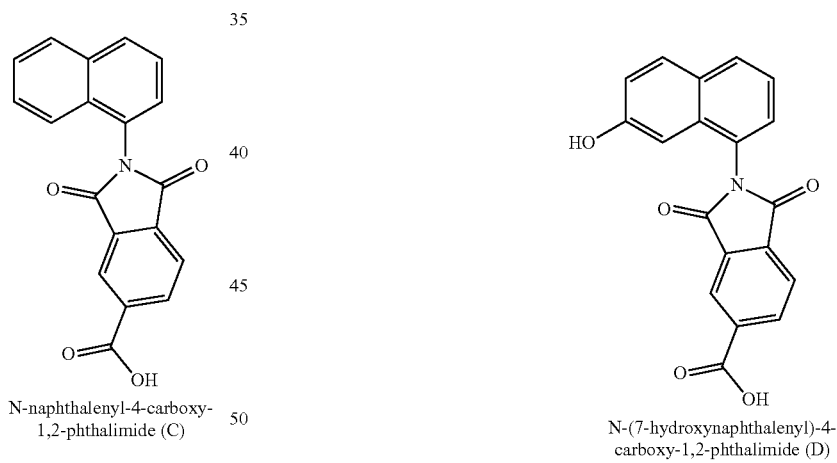
N-naphthalenyl-4-carboxy-
1,2-phthalimide (C)
N-(7-hydroxynaphthalenyl)-4-
carboxy-1,2-phthalimide (D)
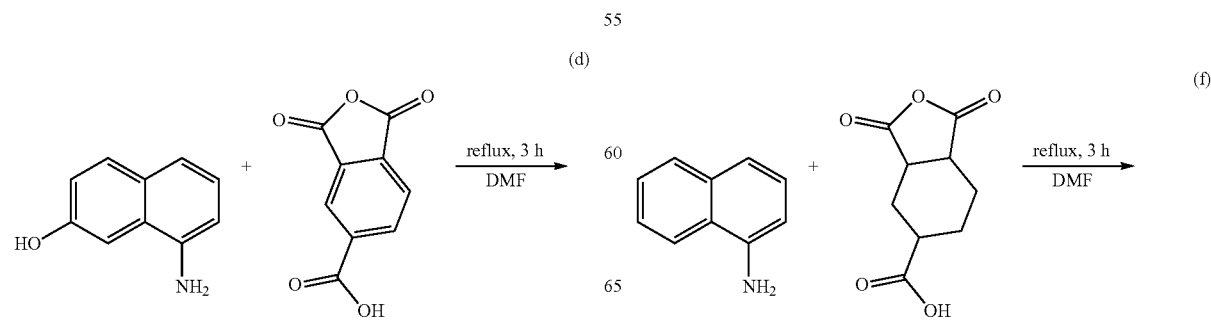

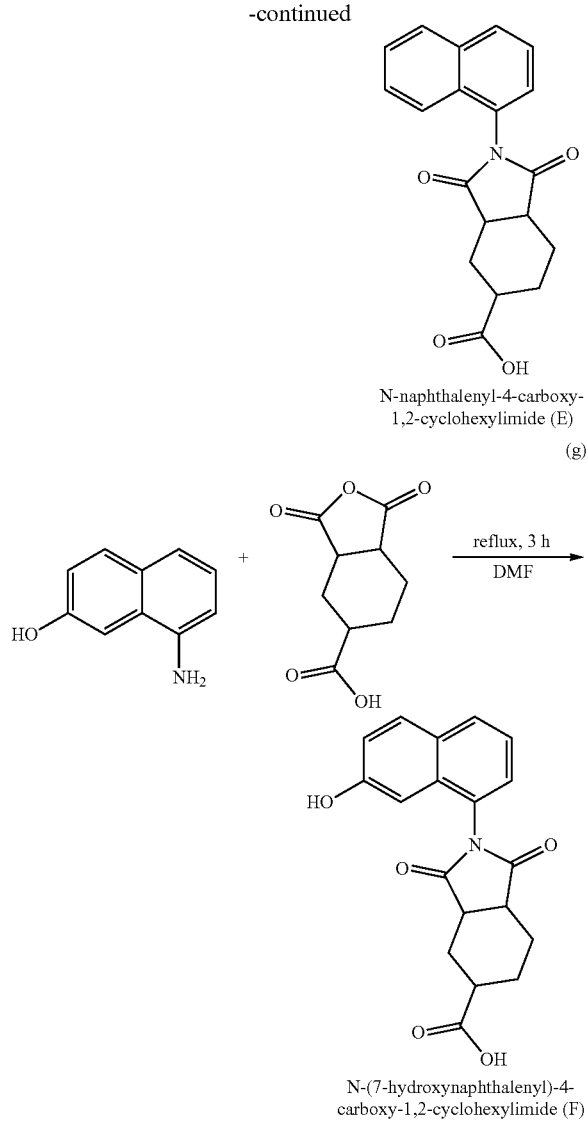

N-naphthalenyl-4-carboxy-1,2-cyclohexylimide (E)

N-(7-hydroxynaphthalenyl)-4-carboxy-1,2-cyclohexylimide (F)

Preparation of N-naphthalenyl-4-carboxy-1,2-phthalimide (Scheme 1a)

A 500 mL round bottom flask was charged with 100 g (0.52 mol) of trimellitic anhydride (source: Sigma Aldrich), 81.98 g (0.57 mol) of 1-naphthylamine (source: Sigma Aldrich) and 65 g of DMF and refluxed for 2.5 h. Upon cooling to room temperature, the mixture was diluted in 300 mL of butyl acetate and precipitated in 500 mL of hexane. The precipitate was filtered off and dried under reduced pressure which resulted in 155 g of yellowish solid product (anchor C).

Preparation of N-naphthalenyl-4-carboxy-1,2-phthalimide (Scheme 1b)

In a 1 L round bottom flask attached with a dean-stark, 100 g (0.52 mol) of trimellitic anhydride (source: Sigma Aldrich), 81.98 g (0.57 mol) of 1-naphthylamine (source: Sigma Aldrich) and 200 g of isopropanol was refluxed for 15 h. The reaction was followed NMR spectroscopy. At the end of the reaction, ~150 g of isopropanol was distilled off by heating at reflux condition. The remaining isopropanol was removed by vacuum to result in 212.94 g (85% solid) of product (anchor C).

Preparation of N-naphthalenyl-4-carboxy-1,2-phthalimide (Scheme 1c)

In a 1 L round bottom flask attached with a dean-stark, 100 g (0.52 mol) of trimellitic anhydride (source: Sigma Aldrich), 81.98 g (0.57 mol) of 1-naphthylamine (source: Sigma Aldrich) and 200 g of MIAK was refluxed for 2.5 h with distillation of water. The progress of the reaction was followed with the amount of water collected in the Dean-stark apparatus. At the end of the reaction, ~150 g of MIAK was distilled off by heating at reflux condition. The remaining solvent was removed under reduced pressure to result in 200 g (91% solid) of product (anchor C).

Preparation of N-(7-hydroxynaphthalenyl)-4-carboxy-1,2-phthalimide (Scheme 1d)

A 250 mL round bottom flask was charged with 50 g (0.26 mol) of trimellitic anhydride (source: Sigma Aldrich), 46.0 g (0.29 mol) of 7-hydroxy 1-naphthylamine (source: Sigma Aldrich) and 60 g of DMF and refluxed for 3 h. Upon cooling to room temperature, the mixture was diluted in 300 mL of butyl acetate and precipitated in 500 mL of hexane. The precipitate was filtered off and dried under reduced pressure which resulted in 85 g (65% solid) of product (anchor D).

Preparation of N-(7-hydroxynaphthalenyl)-4-carboxy-1,2-phthalimide (Scheme 1e)

In a 500 mL round bottom flask attached with a dean-stark, 30.17 g (0.16 mol) of trimellitic anhydride (source: Sigma Aldrich), 25 g (0.16 mol) of 7-hydroxy 1-naphthylamine (source: Sigma Aldrich) and 150 g of MIAK was refluxed for 5 h with distillation of water. The reaction was followed with the amount of water collected in the Dean-stark apparatus. At the end of the reaction, ~50 g of MIAK was distilled off by heating at reflux condition. The remaining MIAK was removed under reduced pressure 87.57 g (63% solid) of product (anchor D).

Preparation of the Di-Block Polymeric Pigment Dispersants
(I) Preparation of Solventborne Di-Block Prepolymer According to methods that are familiar to those skilled in the art, the di-block prepolymer for solventborne dispersants (prepolymer 1, prepolymer 2 and prepolymer 3) were synthesized out via controlled radical polymerization (CRP) in three major steps as described below. The raw material composition is provided in Tables 1-3. The characteristics of different backbones that are used in the synthesis of the random type of polymeric dispersants are shown in Table 4.

Step A: A 5 L four neck round bottom flask fitted with a condenser, an agitator, and a ther-mocouple was charged with reagents 1-4 (Tables 1-2) and purged with nitrogen for 10 minutes. This was followed by addition of reagent 5 with further purging of 20 minutes. The dark brown mixture was heated to 70° C. and held at that temperature for 1.5 h. Nitrogen purging was continued until the temperature reached to 70° C.

Step B: At the end of step A, the temperature of the reaction mixture was reduced to 60° C. and a mixture of reagents 6-9 (Tables 1-2) purged with nitrogen for 30 minutes, was trans-ferred to the reaction flask through a cannula under slight positive nitrogen pressure. The reaction temperature was increased to and held at 80° C. for 9.5 h.

Step C: At the end of step B, the reaction mixture was exposed to air. A mixture of reagents 10 and 11 (Tables 1-2) was added directly to the flask and held at 80° C. for 5 h. Towards the end of this process the green colour of the resin disappeared and the initially yellow amberlyte-748 resin turned into bluish green. The solution was filtered through a solid filtration funnel to remove amberlyte resin beads. The acetic acid and some solvent was distilled off under reduced pressure until 10% of the volatile is removed.

TABLE 1

Synthesis of prepolymer 1

| | | Raw material | Weight (g) | Mol |
|---|---|---|---|---|
| 1 | A | Butyl acetate | 1112.4000 | 9.5764 |
| 2 | | Glycidyl methacrylate | 434.5000 | 3.0565 |
| 3 | | TsCl | 57.2000 | 0.3000 |
| 4 | | Bpy | 9.4490 | 0.0605 |
| 5 | | Cu(0) | 3.8445 | 0.0605 |
| 6 | B | Butyl methacrylate | 406.1200 | 3.1686 |
| 7 | | HPMA | 568.9200 | 3.9462 |
| 8 | | n-butyl acetate | 500.0000 | |
| 9 | | Butyl acrylate | 962.5000 | 7.5096 |
| 10 | C | Acetic acid | 27.4313 | 0.4568 |
| 11 | | Amberlyte-748 | 173.2500 | | where,
glycidyl methacrylate and HPMA=2-hydroxypropyl methacrylate were obtained from Dow Chemical; butyl methacrylate, TsCl=p-toluene sulfonyl chloride, acetic acid and Bpy=bipyridyl were obtained from Sigma Aldrich; butyl acrylate was obtained from BASF and Amberlyte-748 resin was obtained from Alfa Aesar.

TABLE 2

Synthesis of prepolymer 2

| | | Raw material | Weight (g) | Mol |
|---|---|---|---|---|
| 1 | A | Butyl acetate | 1100.0000 | 9.4697 |
| 2 | | Glycidyl methacrylate | 470.0000 | 3.3063 |
| 3 | | TsCl | 114.4000 | 0.6001 |
| 4 | | Bpy | 7.0868 | 0.0454 |
| 5 | | Cu (0) | 2.8834 | 0.0454 |
| 6 | B | Butyl methacrylate | 439.0000 | 3.4251 |
| 7 | | HPMA | 681.30000 | 4.7253 |
| 8 | | n-butyl acetate | 494.0000 | |
| 9 | | Butyl acrylate | 860.0000 | 6.7098 |
| 10 | C | Acetic acid | 27.4313 | 0.4568 |
| 11 | | Amberlyte-748 | 173.2500 | | where,
glycidyl methacrylate and HPMA=2-hydroxypropyl methacrylate were obtained from Dow Chemical; butyl methacrylate, TsCl=p-toluene sulfonyl chloride, acetic acid and Bpy=bipyridyl were obtained from Sigma Aldrich; butyl acrylate was obtained from BASF and Amberlyte-748 resin was obtained from Alfa Aesar.

TABLE 3

Synthesis of prepolymer 3

| | | Raw material | Weight (g) | Mol |
|---|---|---|---|---|
| 1 | A | MIBK | 1100.0000 | 9.4697 |
| 2 | | Glycidyl methacrylate | 470.0000 | 3.3063 |
| 3 | | TsCl | 114.4000 | 0.6001 |
| 4 | | Bpy | 7.0868 | 0.0454 |
| 5 | | Cu(0) | 2.8834 | 0.0454 |
| 6 | B | PEGMEAcrylate$_{480}$ | 291.1100 | 0.6065 |
| 7 | | HPMA | 115.6500 | 0.8021 |
| 8 | | MIBK | 67.5000 | 0.5811 |
| 9 | C | Acetic acid | 8.1600 | 0.1359 |
| 10 | | AMBERLITE IRC748i | 51.9700 | |
| 11 | | MIBK | 30.0000 | 0.2583 | where,
MIBK=methyl isobutyl ketone; glycidyl methacrylate and HPMA=2-hydroxypropyl methacrylate were obtained from Dow Chemical; TsCl=p-toluene sulfonyl chloride, acetic acid, Bpy=bipyridyl and PEGMEAcrylate480=polyethylene glycol methylether acrylate, $M_n$ 480 were obtained from Sigma Aldrich; and Amberlyte-748 resin was obtained from Alfa Aesar.

(II) Preparation of Solventborne Di-Block Polymeric Dispersants

The di-block prepolymer, prepolymer 2 was reacted with anchors C and D (Scheme 1) using a catalytic amount of N,N-dimethyldodecylamine and butyl acetate under reflux condition (115° C.-124° C.) until the Weight per Epoxy (WPE) reached >15,000 to result in light brown transparent solutions dispersant 1 and dispersant 2 (Table 4) at about 50% non-volatile (NV).

(III) Preparation of a Control Di-Block Polymeric Dispersant

Using same procedure above for preparation of solventborne di-block polymeric dispersants, a comparative example of di-block copolymer was prepared by reacting prepolymer 2 with N-methylcarboxy-1,8-naphthalimide that is commercially available to result in dispersant 4 (Table 4).

(IV) Preparation of Waterborne Di-Block Polymeric Dispersant

The di-block prepolymer 3 was reacted with anchor C (Scheme 1) to result in dispersant 3 at 65% solid content. The mixture was heated under reflux condition (115° C.) until the WPE number reached 12,000. The final product was vacuum dried to result in the removal of MIBK. The resultant product was reduced in 50/50 (w/w) butyl cellosolve (source: Eastman Chemical Company) and DI water to result in a brown transparent solution at about 50% non-volatile (NV).

TABLE 4

Composition of final di-block dispersant resins

| Dispersant resin # | Prepolymer# | Anchors | Solvent/s | Anchors wt % (/solid) | Molecular weight |
|---|---|---|---|---|---|
| dispersant 1 | prepolymer 2 | C | Butyl acetate | 23 | $M_n$ = 5,312 $M_w$ = 8,286 PDI = 1.55 |

TABLE 4-continued

Composition of final di-block dispersant resins

| Dispersant resin # | Prepolymer# | Anchors | Solvent/s | Anchors wt % (/solid) | Molecular weight |
|---|---|---|---|---|---|
| dispersant 2 | prepolymer 2 | D | Butyl acetate | 27 | $M_n$ = 5,517<br>$M_w$ = 8,385<br>PDI = 1.52 |
| dispersant 3 | prepolymer 3 | C | Water:butyl cellosolve (50:50) | 25 | $M_n$ = 4,393<br>$M_w$ = 6,106<br>PDI = 1.39 |
| dispersant 4* | prepolymer 2 | N-methyl-carboxy-1,8-naphthalimide | Butyl acetate | 20 | $M_n$ = 5,134<br>$M_w$ = 8,214<br>PDI = 1.60 |

*not within the scope of the invention

Preparation of Random Polymeric Pigment Dispersant (I) Preparation of Glycidyl Functional Polyacrylate Backbone (Acrylic Backbone BB-1 and BB-2)

The glycidyl functional acrylic copolymers for the synthesis of the random type of polymeric dispersants were synthesized by random copolymerization of glycidyl methacrylate (GMA) with other vinyl and/or (meth)acrylate monomers via conventional state of the art free radical polymerization using solution polymerization technique. The important characteristics of these polyacrylates are described in Table 5. 2,2'-Azobis(2-methyl butyronitrile) AMBN was used as thermal initiator. The characteristics of different backbones used in the synthesis of comb type of hyper-dispersants are shown in Table 5.

TABLE 5

| Acrylic backbone | Comonomers Parts by weight (PbW) respectively | Solvent/s (PbW) | % NV (110° C./1 h) | EEW (g/eq) | Molecular weight |
|---|---|---|---|---|---|
| Acrylic-BB-1 | GMA//styrene/EHA/BzMA (67.7/14.6/3.1/14.6) | MIBK | 64.46% | 229.7 | $M_n$ = 2364<br>$M_w$ = 4548<br>PDI = 1.92 |
| Acrylic-BB-2 | GMA//styrene/EHA (88.5/9.4/2.1) | MIBK | 65.51% | 175.9 | $M_n$ = 2491<br>$M_w$ = 4599<br>PDI = 1.85 | where,
PbW=Parts by Weight
GMA=glycidyl methacrylate (source: Mitsubishi Gas Chemical Company); MMA=methyl methacrylate; UMA=ureido methacrylate (used as 25% W/W solution in MMA) (source: BASF); EHA=ethyl hexyl acrylate (source: Sigma Aldrich); BzMA=benzyl methacrylate (source: Geo Specialty Chemical Company); MIBK=methyl isobutyl ketone (source: Sigma Aldrich).

(II) Preparation of Solventborne Random Type Polymeric Dispersant (Dispersant 5)

Step-1: Synthesis of the Anchor Grafted Intermediate:

According to methods familiar to those skilled in the art, the glycidyl functional acrylic copolymer (Acrylic-BB-1) (36.3 g) was reacted with the anchor D (30.5 g) in the presence of a catalytic amount of zinc acetylacetonate at 110–115° C. until almost all the epoxy groups were consumed as confirmed by FTIR spectroscopy. The reaction mass was cooled to ambient condition and diluted by adding ethyl methyl ketone (60 g) while cooling.

Step-2: Grafting-from of Polyester Side Chains:

According to methods familiar to those skilled in the art, linear polyester stabilization chains are 'grafted from' the anchor grafted intermediate in above step-1 by ring opening polymerization of lactone monomers. The intermediate is gradually heated to 125° C. while distilling out the solvent present in the intermediate. A mixture of ε-caprolactone (132.1 g) and δ-valerolactone (29.0 g) was run into the reactor along with tin(II) 2-ethylhexanoate (0.54 g) while maintaining the temperature between 120° C.-130° C. The reaction was further continued at 125° C. until the desired conversion of lactone was achieved as confirmed by measuring % NV as compared to the theoretical anticipated values. Upon achieving the desired conversion, the mass was cooled to 75° C. and diluted by n-butyl acetate and stirred until a homogeneous solution was observed. The final % NV of the dispersant was 60.8%.

(III) Preparation of Solventborne Random Type Polymeric Dispersant (Dispersant 6)

Step-1: Synthesis of the Anchor Grafted Intermediate:

According to methods familiar to those skilled in the art, the glycidyl functional acrylic copolymer (Acrylic-BB-1) (36.9 g) was reacted with the anchor C (24.05 g) in the presence of a catalytic amount of zinc acetylacetonate at 115° C.-120° C. until almost all the epoxy groups were consumed. The reaction mass was cooled to ambient condition and diluted by adding ethyl methyl ketone (10 g) while cooling.

Step-2: Grafting-from of Polyester Side Chains:

According to methods familiar to those skilled in the art, linear polyester stabilization chains were 'grafted from' the anchor grafted intermediate in above step-1 by ring opening polymerization of lactone monomers. The intermediate was gradually heated to 125° C. while distilling out the solvent that was present in the intermediate. The mixture of ε-caprolactone (118.5 g) and δ-valerolactone (26.0 g) was run into the reactor along with tin(II) 2-ethylhexanoate (0.48 g) while maintaining the temperature between 105° C.-125° C. The reaction was further continued at 120° C. until the desired conversion of lactone was achieved as confirmed by measuring % NV as compared to the theoretical anticipated values. Upon achieving the desired conversion, the mass was cooled to 75° C. and diluted by n-butyl acetate and stirred until a homogeneous solution was observed. The final % NV of the dispersant was 61.7%.

(IV) Preparation of Waterborne Random Type Polymeric Dispersant (Dispersant 7)

The polyethylene glycol (Carbowax 2000 ®) (158.2 g) was charged to the reactor and heated to 120° C. under vacuum and maintained for 30 min. Vacuum was stopped and succinic anhydride (7.5 g) was added and reacted at 118° C.-120° C. for 3.5 h. The glycidyl functional acrylic copolymer (Acrylic-BB-2) (69.9 g) was added followed by the anchor C (48.4 g) in the presence of catalytic amounts of zinc acetylacetonate at 115° C. until almost all the epoxy groups were consumed (epoxy equivalent weight >15000 g/eq). The solvent present in the system was distilled out during the process by simple distillation. While cooling the reaction mass to ambient condition the mass was diluted by adding a mixture of ethyl methyl ketone (112 g) and 1-propoxy-2-propanol (28 g) while stirring. The final % NV of the dispersant was 66.5%.

TABLE 6

Composition of the final random polymeric pigment dispersant resins

| Resin # | polyacrylate backbone | Anchor | Solvent/s | Anchor wt. % (/solid) |
|---|---|---|---|---|
| Dispersant 5 | Acrylic-BB-1 | D | n-butyl acetate | 12.87% |
| Dispersant 6 | Acrylic-BB-2 | C | n-butyl acetate | 12.57% |
| Dispersant 7 | Acrylic-BB-2 | C | ethyl methyl ketone: 1-propoxy-2-propanol; (80:20) | 18.75% |

Blue 7081 D. The pigments were obtained from Sun Chemical, New Jersey, USA and BASF Corporation, New Jersey, USA.

1) Formulation

For solventborne trials, 10% pigment loading with various dispersant on pigment (DoP) concentrations was explored. DoP concentrations ranged from ~30%-~300%. The samples were evaluated in normal butyl acetate (Nexeo Solutions, Warren, Michigan, USA). Table 7 shows typical formulations of synthesized dispersants with ~50% DoP.

For waterborne trials, 10% pigment loading with various dispersant on pigment (DoP) concentrations was explored. DoP concentrations ranged from ~25%-~200%. The samples were evaluated in deionized water and deionized water/solvent mixtures, where the solvent component was at least 2.5 wt. % of the total formulation. Examples of the solvent used include, but are not limited to, propylene glycol n-propyl ether (Nexeo Solutions, Warren, Michigan, USA) and propylene glycol n-butyl ether (Dowanol PNB, The Dow Chemical Company, Midland, Michigan, USA).

2) Grinding

To each formulation, 0.3 mm zirconium stabilized yttria beads (Fox Industries, Fairfield, New Jersey, USA) were added in order to grind the pigment. For solventborne systems, the beads were ~100% of the total formulation weight, for example 100 g of formulation was added to 100 g of beads to make a total of 200 g. For waterborne systems, the beads were 200% of the total formulation weight, for example 100 g of formulation was added to 200 g of beads to make a total of 300 g.

The prepped sample was then placed on the Lau Disperser—Model DAS H-TP 200-K with cooling system (LAU GmbH, Hemer, Germany) and shaken with the fan on for 540 minutes or 9 hours. Upon completion of the run, the samples were filtered to remove the beads and stored in aluminium paint cans. Filtered beads were washed with solvent and reused.

TABLE 7

Composition of the pigment dispersions

|  | Example 1 | Example 2 | Example 3 | Example 4 | Example 5 | Example 6 | Example 7* | Example 8* | Example 9* |
|---|---|---|---|---|---|---|---|---|---|
| dispersant 1 | 9.86 |  | 9.86 |  | 9.86 |  |  |  |  |
| dispersant 2 |  | 10.1 |  | 10.1 |  | 10.1 |  |  |  |
| dispersant 4* |  |  |  |  |  |  | 9.84 | 9.84 | 9.84 |
| 229-6438 (maroon) |  |  | 10 | 10 |  |  |  | 10 |  |
| L3920 (red) | 10 | 10 |  |  |  |  | 10 |  |  |
| L3990 (maroon) |  |  |  |  | 10 | 10 |  |  | 10 |
| n-butyl acetate | 80.14 | 79.90 | 80.14 | 79.90 | 80.14 | 79.90 | 80.16 | 80.16 | 80.16 |
| Total | 100 | 100 | 100 | 100 | 100 | 100 | 100 | 100 | 100 |

*not within the scope of the invention

Evaluation and Observation of the Polymeric Dispersants

In order to evaluate the polymeric dispersants synthesized according to the process described hereinabove, solventborne and waterborne samples were formulated and ground using a Lau Disperser. The sample grind, colour performance and the particle size distribution were measured.

The evaluation was done with multiple high performance organic pigments for coatings that include, but are not limited to, BASF Perrindo Maroon L3920, BASF Perrindo Maroon L 39990, Sun Chemical Perrindo Maroon 229-8801, Sun Chemical Perrindo Maroon 229-6438, Sun Chemical Perrindo Violet 29, Clariant Hostaperm Brown HFR01, Sun Chemical Palomar Blue 248-4816, and BASF Heliogen Evaluation of Stability and Colour 1) Sample Stability After filtration, the fineness of the grind was evaluated using a Hegman gauge. Samples were considered to be passing if they showed a grind of <6 micron.

2) Colour Evaluation

The solventborne pigment dispersions were evaluated for colour performance in R10CG0392D, a commercially available 1 component clear coat from BASF Corp. at 26701 Telegraph Rd. Southfield, Michigan 48033 using melinex drawdown sheets (Puetz GmbH+CO. Fo-lien KG, Taunusstein, Germany). The pigments (L3920, L3990, 229~6438) were evaluated at 0.3% pigment to binder ratio by weight. The binder weight included only the 51% solids from the clearcoat. Pigment was added to R10CG0392D clearcoat under agitation. A 150 μm gap on the Byk drawdown bar was used (Byk-Chemie GmbH, Wesel, Germany) and allowed to flash for ~20 minutes. The sample was subsequently baked for 20 minutes at 270° F. Samples were made in duplicate to ensure reproducibility.

Once the sample cooled, the colour spectrum was measured using a Byk Mac i spectrophotometer (Byk-Chemie GmbH, Wesel, Germany). The melinex card with the tinted clearcoat drawdown was placed on top of a reflective mirror. The Byk Mac i is then placed on top of the melinex and mirror and colour data measured with d65 light at 15, 25, 45, 75, and 110 degrees off specular using GM CieLab weightings. Measurements were done five times per sample and replicate drawdowns of a given sample compared.

This method is used for colour evaluation because higher particle size pigment agglomerates resulting in more scattered light which increases the measured lightness values of the film. As the 110° angle has the longest film path length, it is the most sensitive to detecting increases in scattering. Therefore, L* values (lightness) at the 110° angle were used for evaluation, whereby dispersions yielding lower L* values are more transparent and resemble therefore an improved distribution or stabilization or dispersion of the pigment particles.

Table 8 provides typical L* values at the 110° angle for the formulated systems in Table 7.

TABLE 8

|  | L* at 110° | <dL> at 110° |
|---|---|---|
| Example 1 | 10.22 | −0.88 |
| Example 2 | 10.01 | −1.16 |
| Example 3 | 11.57 | −1.84 |
| Example 4 | 11.59 | −1.82 |
| Example 5 | 11.95 | −1.41 |
| Example 6 | 12.41 | −0.84 | where,
L* is lightness value at 110°;
<dL> is the weighted value of the difference in L* at 110° between a reference dispersion, i.e. dispersion composition with dispersant 4 (Examples 7*, 8* and 9*, with the anchor group as N-methylcarboxy-1,8-naphthalimide) and the dispersions with polymeric pigment dispersants of the presently claimed invention (Examples 1 to 6).

Discussion of Results

The results in the Table 8 shows that the Examples 1~6 with polymeric pigment dispersants of the presently claimed invention show lower L* values. A negative value of <dL> indicates that the polymeric pigment dispersant has a lower L* value than the reference dispersion. This is also indicative that the dispersions with the polymeric pigment dispersants of the presently claimed invention are more transparent than the reference dispersion.

Within each pigment type there is good correlation between smaller particle size and de-creased lightness values at 1100 related to scattering and opacity. A lower L* value generally correlates to smaller particle size.

Advantages
1) The di-block polymeric dispersants of the presently claimed invention provide more efficient de-agglomeration over the dispersant made from the anchor molecule N-methylcarboxy-1,8-naphthalimide which was also prepared by the Controlled Radical Polymerization (CRP) method with di-block prepolymer. This indicates that more chromatic and transparent colour can be achieved via high energy micro milling process to result in pigment particles to less than 100 nm size range.

2) The new anchors (formula IV) of the presently claimed invention are compatible with clearcoat coating compositions which contains organic acid catalyst. This is an advantage over the commercial dispersants that contain amines which reacts with the acid catalyst and loses the dispersing ability.

Test Methods
L* Value Determination

The L* value was determined using Byk Mac i spectrophotometer (Byk-Chemie GmbH, Wesel, Germany). The colour data was measured with a D65 light source, and weighted dL or <dL> values were determined using GM CieLab weightings according to the standard DIN 6175~2.

Weight Per Epoxy (WPE) Determination

The WPE was determined by titration with hydrogen bromide (HBr) according to ASTM D1652.

Non-Volatile (NV) Determination

The NV was determined in accordance with ASTM D2369 by removing the volatile component in a forced air draft oven set at 110° C. to 60 minutes.

The invention claimed is:
1. A polymeric pigment dispersant comprising a polymer backbone (P) and at least one moiety of a formula (I):

wherein
R1 is selected from the group consisting of naphthyl, anthracenyl and phenanthrenyl which are unsubstituted or substituted with 1, 2, 3, 4 or 5 substituents independently of each other, selected from the group consisting of F, Cl, Br, I, —NO$_2$, —CN, —OH, —O—C$_1$-C$_6$-alkyl, —C(=O)-C$_1$-C$_6$-alkyl, —C(=O)—O—C$_1$-C$_6$-alkyl, —C(=O)-O-phenyl, —CH$_2$-C(=O)-C$_1$-C$_6$-alkyl, —C(=O)-NH(C$_1$-C$_6$)alkyl, —C(=O)-NH-phenyl, and -C$_1$-C$_6$-alkyl; wherein—C$_1$C$_6$-alkyl is itself unsubstituted or substituted with 1, 2, 3, 4 or 5 substituents independently of each other, selected from the group consisting of F, Cl, Br, I, —CN, —OH, —O—CF$_3$, —O—CH$_3$ and —O—C$_2$H$_5$;
R$_2$ is selected from the group consisting of a hydrogen; a linear or a branched, substituted C$_1$-C$_{14}$ alkyl substituted with one —C(=O)—O-group, and a linear or a branched, substituted C$_2$-C$_{14}$ alkenyl substituted with one —C(=O)—O-group;
R$_3$ is selected from the group consisting of a linear or a branched, substituted C$_1$-C$_{14}$ alkyl and a linear or branched, substituted C$_2$-C$_{14}$ alkenyl, which are each substituted with one —C(=O)—O-group; or
R$_2$ and R$_3$ together with the carbon atoms to which they are bonded form a substituted phenyl or a substituted C$_3$-C$_{10}$ cycloalkyl or a substituted C$_4$-C$_{10}$ cycloalkenyl, which are each substituted with one —C(=O)—O-group; and whereby the at least one moiety of the formula (I) is bonded to the polymer backbone (P) via the —C(=O)—O-group.

2. The polymeric pigment dispersant according to claim 1, wherein the at least one moiety of the formula (I) is obtained by reacting at least one compound of formula (II)

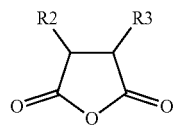

wherein
R$_2$ is selected from the group consisting of a hydrogen; a linear or a branched, substituted C$_1$-C$_{14}$ alkyl substituted with one —C(=O)—OH group, and a linear or a branched, substituted C$_2$-C$_{14}$ alkenyl substituted with one —C(=O)—OH group;
R$_3$ is selected from the group consisting of a linear or a branched, substituted C$_1$-C$_{14}$ alkyl and a linear or branched, substituted C$_2$-C$_{14}$ alkenyl, which are each substituted with one —C(=O)—OH group; or
R$_2$ and R$_3$ together with the carbon atoms to which they are bonded form a substituted phenyl or a substituted C$_3$-C$_{10}$ cycloalkyl or a substituted C$_4$-C$_{10}$ cycloalkenyl which are each substituted with one —C(=O)—OH group;
with at least one compound of formula (III)

 (III)

wherein
R1 is selected from the group consisting of naphthyl, anthracenyl and phenanthrenyl which are unsubstituted or substituted with 1, 2, 3, 4 or 5 substituents independently of each other, selected from the group consisting of F, Cl, Br, I, —NO$_2$, —CN, —OH, —O—C$_1$-C$_6$-alkyl, —C(=O)-C$_1$-C$_6$-alkyl, —C(=O)—O—C$_1$-C$_6$-alkyl, —C(=O)-O-phenyl, —CH$_2$-C(=O)-C$_1$-C$_6$-alkyl, —C(=O)-NH(C$_1$-C$_6$)alkyl, —C(=O)-NH-phenyl, and -C$_1$-C$_6$-alkyl; wherein—C$_1$C$_6$-alkyl is itself unsubstituted or substituted with 1, 2, 3, 4 or 5 substituents independently of each other, selected from the group consisting of F, Cl, Br, I, —CN, —OH, —O—CF$_3$, —O—CH$_3$ and —O—C$_2$H$_5$;
optionally in the presence of at least one solvent.

3. The polymeric pigment dispersant according to claim 1, wherein the polymer backbone (P) is a linear di-block polymer.

4. The polymeric pigment dispersant according to claim 1, wherein the polymer backbone (P) is a random polymer.

5. The polymeric pigment dispersant according to claim 4, wherein the polymeric pigment dispersant is a graft polymer.

6. A process for a preparation of at least one polymeric pigment dispersant comprising at least the steps of:
reacting a linear di-block polymer with a compound of a formula (IV):

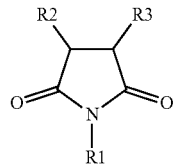 (IV)

wherein
R1 is selected from the group consisting of naphthyl, anthracenyl and phenanthrenyl which are unsubstituted or substituted with 1, 2, 3, 4 or 5 substituents independently of each other, selected from the group consisting of F, Cl, Br, I, —NO$_2$, —CN, —OH, —O—C$_1$-C$_6$-alkyl, —C(=O)-C$_1$-C$_6$-alkyl, —C(=O)—O—C$_1$-C$_6$-alkyl, —C(=O)-O-phenyl, —CH$_2$-C(=O)-C$_1$-C$_6$-alkyl, —C(=O)-NH(C$_1$-C$_6$)alkyl, —C(=O)-NH-phenyl, and -C$_1$-C$_6$-alkyl; wherein—C$_1$C$_6$-alkyl is itself unsubstituted or substituted with 1, 2, 3, 4 or 5 substituents independently of each other, selected from the group consisting of F, Cl, Br, I, —CN, —OH, —O—CF$_3$, —O—CH$_3$ and —O—C$_2$H$_5$;
R$_2$ is selected from the group consisting of a hydrogen; a linear or a branched, substituted C$_1$-C$_{14}$ alkyl substituted with one —C(=O)—OH group, and a linear or a branched, substituted C$_2$-C$_{14}$ alkenyl substituted with one —C(=O)—OH group;
R$_3$ is selected from the group consisting of a linear or a branched, substituted C$_1$-C$_{14}$ alkyl and a linear or branched, substituted C$_2$-C$_{14}$ alkenyl, which are each substituted with one —C(=O)—OH group; or
R$_2$ and R$_3$ together with the carbon atoms to which they are bonded form a substituted phenyl or a substituted C$_3$-C$_{10}$ cycloalkyl or a substituted C$_4$-C$_{10}$ cycloalkenyl, which are each substituted with one —C(=O)—OH group;
at a temperature from ≥80° C. to ≤150° C.; and
wherein the linear di-block polymer comprises a first and a second block and is obtained by a living free radical polymerization, optionally in the presence of a solvent.

7. A process for a preparation of at least one polymeric pigment dispersant comprising at least the steps of:
(a) reacting a random polymer with a compound of a formula (IV):

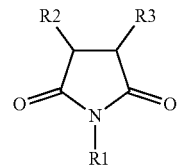 (IV)

wherein
R1 is selected from the group consisting of naphthyl, anthracenyl and phenanthrenyl which are unsubstituted or substituted with 1, 2, 3, 4 or 5 substituents independently of each other, selected from the group consisting of F, Cl, Br, I, —NO$_2$, —CN, —OH, —O—C$_1$-C$_6$-alkyl, —C(=O)-C$_1$-C$_6$-alkyl, —C(=O)—O—C$_1$-C$_6$-alkyl, —C(=O)-O-phenyl, —CH$_2$-C(=O)-C$_1$-C$_6$-alkyl, —C(=O)-NH(C$_1$-C$_6$)alkyl, —C(=O)-NH-phenyl, and -C$_1$-C$_6$-alkyl; wherein—C$_1$C$_6$-alkyl is itself unsubstituted or substituted with 1, 2, 3, 4 or 5 substituents independently of each other, selected from the group consisting of F, Cl, Br, I, —CN, —OH, —O—CF$_3$, —O—CH$_3$ and —O—C$_2$H$_5$;
R$_2$ is selected from the group consisting of a hydrogen; a linear or a branched, substituted C$_1$-C$_{14}$ alkyl substituted with one —C(=O)—OH group, and a linear or a branched, substituted C$_2$-C$_{14}$ alkenyl substituted with one —C(=O)—OH group;
R$_3$ is selected from the group consisting of a linear or a branched, substituted C$_1$-C$_{14}$ alkyl and a linear or branched, substituted $C_2$-$C_{14}$ alkenyl, which are each substituted with one —C(═O)—OH group; or $R_2$ and $R_3$ together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(═O)—OH group; and (b) reacting the compound obtained in step (a) with at least one monomer of a lactone at a temperature from ≥30° C. to ≤190° C.

8. A process for a preparation of at least one polymeric pigment dispersant comprising at least the steps of:
(a) reacting at least one polyalkylene glycol monoalkyl ether and at least one carboxylic acid anhydride at a temperature in a range from ≥70° C. to ≤140° C. to obtain a mixture; and
(b) reacting the mixture obtained in step (a) with a random polymer and a compound of a formula (IV):

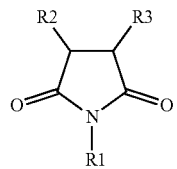

(IV)

wherein
R1 is selected from the group consisting of naphthyl, anthracenyl and phenanthrenyl which are unsubstituted or substituted with 1, 2, 3, 4 or 5 substituents independently of each other, selected from the group consisting of F, Cl, Br, I, —$NO_2$, —CN, —OH, —O—$C_1$-$C_6$-alkyl, —C(═O)-$C_1$-$C_6$-alkyl, —C(═O)—O—$C_1$-$C_6$-alkyl, —C(═O)-O-phenyl, —$CH_2$-C(═O)-$C_1$-$C_6$-alkyl, —C(═O)-NH($C_1$-$C_6$)alkyl, —C(═O)-NH-phenyl, and -$C_1$-$C_6$-alkyl; wherein—$C_1C_6$-alkyl is itself unsubstituted or substituted with 1, 2, 3, 4 or 5 substituents independently of each other, selected from the group consisting of F, Cl, Br, I, —CN, —OH, —O—$CF_3$, —O—$CH_3$ and —O—$C_2H_5$;

$R_2$ is selected from the group consisting of a hydrogen; a linear or a branched, substituted $C_1$-$C_{14}$ alkyl substituted with one —C(═O)—OH group, and a linear or a branched, substituted $C_2$-$C_{14}$ alkenyl substituted with one —C(═O)—OH group;

$R_3$ is selected from the group consisting of a linear or a branched, substituted $C_1$-$C_{14}$ alkyl and a linear or branched, substituted $C_2$-$C_{14}$ alkenyl, which are each substituted with one —C(═O)—OH group; or $R_2$ and $R_3$ together with the carbon atoms to which they are bonded form a substituted phenyl or a substituted $C_3$-$C_{10}$ cycloalkyl or a substituted $C_4$-$C_{10}$ cycloalkenyl, which are each substituted with one —C(═O)—OH group;

at a temperature in a range from ≥70° C. to ≤140° C.

9. A pigment dispersion comprising at least one polymeric pigment dispersant according to claim 1, at least one solvent and at least one pigment.

10. A coating composition comprising the pigment dispersion according to claim 9 and at least one binder.

11. A printing ink, an automotive basecoat, an automotive clearcoat, a mill base, a furniture coating or a wood coating, comprising the pigment dispersion according to claim 9.

12. An article coated with at least one layer formed from the coating composition according to claim 10.

* * * * *